United States Patent
Nishimura et al.

(10) Patent No.: US 10,167,269 B2
(45) Date of Patent: Jan. 1, 2019

(54) COCKROACH ATTRACTION-AGGREGATION SUBSTANCE, COCKROACH AGGREGATION ATTRACTANT AND COCKROACH CONTROLLING AGENT

(71) Applicants: Kyoto University, Kyoto (JP); Dainihon Jochugiku Co., Ltd., Osaka (JP)

(72) Inventors: Yukihiro Nishimura, Kyoto (JP); Masayuki Sakuma, Kyoto (JP); Tamio Ueno, Osaka (JP); Noritada Matsuo, Osaka (JP); Yasuyuki Koutani, Osaka (JP)

(73) Assignees: Kyoto University, Kyoto (JP); Dainihon Jochugiku Co., Ltd., Osaka (JP)

( * ) Notice: Subject to any disclaimer, the term of this patent is extended or adjusted under 35 U.S.C. 154(b) by 0 days.

(21) Appl. No.: 15/107,801

(22) PCT Filed: Dec. 18, 2014

(86) PCT No.: PCT/JP2014/083519
§ 371 (c)(1),
(2) Date: Jun. 23, 2016

(87) PCT Pub. No.: WO2015/098681
PCT Pub. Date: Jul. 2, 2015

(65) Prior Publication Data
US 2016/0326129 A1   Nov. 10, 2016

(30) Foreign Application Priority Data

Dec. 26, 2013 (JP) .................. 2013-269632

(51) Int. Cl.
C07D 311/74 (2006.01)
A01N 43/12 (2006.01)
A01N 43/16 (2006.01)
C07D 307/88 (2006.01)

(52) U.S. Cl.
CPC ............ *C07D 311/74* (2013.01); *A01N 43/12* (2013.01); *A01N 43/16* (2013.01); *C07D 307/88* (2013.01)

(58) Field of Classification Search
CPC .... C07D 311/74; C07D 307/88; A01N 43/12; A01N 43/16
See application file for complete search history.

(56) References Cited

U.S. PATENT DOCUMENTS

| 5,332,717 | A | * | 7/1994 | Luthy ................ A01N 43/54 504/196 |
| 5,428,002 | A | | 6/1995 | Lüthy et al. |
| 5,505,951 | A | | 4/1996 | Roelofs et al. |
| 6,074,634 | A | | 6/2000 | Lopez, Jr. et al. |

FOREIGN PATENT DOCUMENTS

| CN | 103408528 A | 11/2013 |
| JP | 61-69747 | 4/1986 |
| JP | 4-504265 | 7/1992 |
| JP | 05-097841 A | 4/1993 |
| JP | 6-24923 | 2/1994 |
| JP | 6-25279 | 2/1994 |
| JP | 08-268889 A | 10/1996 |
| JP | 2002-284610 | 10/2002 |
| WO | WO 2011/051225 A1 | 5/2011 |
| WO | WO 2012/166617 A2 | 12/2012 |

OTHER PUBLICATIONS

Roberts et al. "Studies in Mycological Chemistry. Part XXIV. Synthesis of Ochratoxin A, a Metabolite of Aspergillus ochraceus Wilh." J. Chem. Soc. (C), 1970, 2, 278-281.*
Achenbach, Hans et al., "Phthalide and Chromanole aus Aspergillas duricaulis" Liebigs Annalen der Chemie, 1985, pp. 1596-1628—Abstract.
Barber, Jill et al., "The Total Synthesis of some Deuterium Labelled Pentaketide Derivatives of Orsellinic Acid" Journal of the Chemical Society, Perkin Transactions 1: Organic and Bio-Organic Chemistry, 1981, pp. 1685-1689.
Bestmann, Hans Jürgen et al., "3,4-Dihydroisocumarine, eine neue Klasse von Spurpheromonen bei Ameisen" Angew. Chem., 1992, pp. 757-758, vol. 104, No. 6.
Bestmann, Hans Jürgen et al., "3,4-Dihydroisocoumarins, a New Class of Ant Trail Pheromones" Angewandte Chemie International Edition in English, 1992, pp. 795-796, vol. 31, No. 6.
Boulangé, Agathe et al., "Diastereoselective IBX Oxidative Dearomatization of Phenols by Remote Induction: Towards the Epicocconone Core Framework" Chemistry European Journal, 2011, pp. 10241-10245, vol. 17, No. 37.
Bruce, J. Malcolm et al., "Benzoquinones and Related Compounds. Part 2.[1] Preferred Conformations of Some Acyl-1,4-benzoquinones in Solution" Journal of the Chemical Society, Perkin Transactions 2: Physical Organic Chemistry, 1980, pp. 860-866, vol. 6.
Duncanson, L.A. et al., "Gladiolic Acid. Part III. The Structures of Norisogladiolic Acid, Dihydrogladiolic Acid, and Cyclopolic Acid" Journal of the Chemical Society, 1953, pp. 3637-3645.
Feige, G.B. et al., "Identification of lichen substances by a standardized high-performance liquid chromatographic method" Journal of Chromatography, 1993, pp. 417-427, vol. 646.
Gainsford, Graeme J. "Antifungal Compounds Isolated from New Zealand Flax: 7-Hydroxy-5-methoxy-6-methylphthalide and 4-Methoxycarbonyl-β-orcinol" Acta Crystallographica, 1995, pp. 709-712, vol. C51.
Hashmi, A. Stephen K. et al., "Gold catalysis: five new bonds by a domino hydroarylation/cycloisomerization" Tetrahedron, 2005, pp. 6231-6236, vol. 61.

(Continued)

*Primary Examiner* — Yong S. Chong
(74) *Attorney, Agent, or Firm* — Knobbe, Martens, Olson & Bear, LLP

(57) ABSTRACT

Provided is a solution for the problems associated with cockroach aggregation pheromones and cockroach aggregation attractants or cockroach controlling agents containing cockroach aggregation pheromones. In particular, provided is a compound serving as a cockroach attraction-aggregation substance, the compound being represented by general formula or a salt thereof.

4 Claims, 8 Drawing Sheets

(56) References Cited

OTHER PUBLICATIONS

Holler, Ulrich et al., "Fungi from marine sponges: diversity, biological activity and secondary metabolites" Mycological Research, Nov. 2000, pp. 1354-1365, vol. 104, No. 11.
Hussain, Ibrar et al., "Synthesis of Dibenzo[b,d]pyran-6-ones Based on [3+3] Cyclizations of 1,3-Bis(silyl enol ethers) with 3-Silyloxy-2-en-1-ones" J. Org. Chem., 2007, pp. 6255-6258, vol. 72.
Isaev, I.S. et al., "Transformations of pentamethylbenzoic acid and its derivatives during nitration" Zhurnal Organicheskoi Khimii, 1971, pp. 2321-2326, vol. 7, No. 11—Abstract.
Jütten, Peter et al., "Thiosemicarbazones of Formyl Benzoic Acids as Novel Potent Inhibitors of Estrone Sulfatase" J. Med. Chem., 2007, pp. 3661-3666, vol. 50.
Kubota, T. et al., "Structures of Sclerin and Sclerolide, Metabolites of Sclerotinia Libertiana" Tetrahedron Letters, 1966, pp. 5205-5210, No. 42.
Kuramata, Masato et al., "Citrinolactones A, B and C, and Sclerotinin C, Plant Growth Regulators from Penicillium citrinum" Bioscience Biotechnology and Biochemistry, 2007, pp. 499-503, vol. 71, No. 2.
Langer, Peter et al., "Efficient synthesis of biaryl lactones by domino retro-Michael-aldol-lactonization reactions" Chemical Communications, 2002, pp. 168-169, vol. 2.
Langer, Peter et al., "Efficient synthesis of benzopyrano[2,3-b]pyridines by sequential reactions of 1,3-bis-silylenol ethers with 3-cyanobenzopyrylium triflates" Tetrahedron Letters, 2003, pp. 5133-5135, vol. 44, No. 27.
Luo, Shi-Lin et al., "Isocoumarins from American cockroach (*Periplaneta americana*) and their cytotoxic activities" Fitoterapia, 2014, pp. 115-120, vol. 95.
Mali, Raghao S. et al., "Novel $AlCl_3$ Catalysed Syntheses of Naturally Occurring (±) 8-Hydroxy-3-methyl-3,4-dihydroisocoumarins" Journal of the Chemical Society, Chemical Communications, 1992, pp. 883-884, vol. 12.
Matsui, Masanao et al., "Synthesis of Isochroman-I,3-diones—A New Synthesis of (±)Sclerin" Agricultural and Biological Chemistry, 1968, pp. 492-495, vol. 32, No. 4.
Momose, Tsutomu et al., "Studies on Tetralin Derivatives. I. Bacteriostatic Activity in vitro" Pharmaceutical Bulletin, 1954, pp. 119-122, vol. 2.
Mühlenfeld, Andreas et al., "Asperdurin, ein neues antimykotisches Phthalid aus Aspergillus duricaulis" Archiv der Pharmazie, 1988, pp. 803-805, vol. 321, No. 11—Abstract.
Nagaoka, Hiroto et al., "A Synthesis of the Aromatic Segment of Rifamycin S" Tetrahedron Letters, 1981, pp. 899-902, vol. 22.
Naito, Shinsuke et al., "Two New Phenolic Reductones from Aspergillus Terreus" Tetrahedron Letters, 1969, pp. 4675-4678, vol. 53.
Pundt, Thomas "One-pot synthesis of aryl fluorides by [3+3] cyclization of 1,3-bis(silyl enol ethers) with 2-fluoro-3-silyloxy-2-en-1-ones" Tetrahedron Letters, 2007, pp. 2745-2747, vol. 48.
Saeed, Aamer et al., "Synthesis of 3,4-Dihydro-8-hydroxy-6-methoxy-7-methylisocoumarin and (±)-6,8-Dimethoxy-1,7-dimethylisochroman" Journal of the Chemical Society of Pakistan, 1993, pp. 212-215, vol. 15, No. 3.
Shan, R. et al., "Naphthalenone and Phthalide Metabolites from Lachnum papyraceum" Journal of Natural Products, 1997, pp. 804-805, vol. 60, No. 8.
Sommart, Ubonta et al., "Modiolin and phthalide derivatives from the endophytic fungus *Microsphaeropsis arundinis* PSU-G18" Tetrahedron, 2012, pp. 10005-10010, vol. 68, No. 48.
Suzuki, Akinori et al., "Aggregation pheromones" Nougei Kagaku no Jiten, 2003, pp. 183-186.
Takahashi, Kosaku et al., "Novel Antifungal Compounds Produced by Sterile Dark, an Unidentified Wheat Rhizosphere Fungus" Bioscience Biotechnology and Biochemistry, 2005, pp. 1018-1020, vol. 69, No. 5.
Takatori, Masayuki et al., "On the Trimorphism of 7-Hydroxy-3-(p-methoxyphenyl)-4,6-dimethyl-1-indanone" Bulletin of the Chemical Society of Japan, 1975, pp. 3411-3412, vol. 48, No. 11.
Tokoroyama, Takshi et al., "Syntheses of Sclerin Analogs" Nippon Kagaku Kaishi, 1974, pp. 136-146, vol. 1—Abstract.
Ullah, Ihsan et al., "Chelation-control in the formal [3+3] cyclization of 1,3-bis-(silyloxy)-1,3-butadienes with 1-hydroxy-5-silyloxy-hex-4-en-3-ones. One-pot synthesis of 3-aryl-3,4-dihydroisocoumarins" Tetrahedron, 2010, pp. 1874-1884, vol. 66.
Zhou, Zhong-Yu et al., "Two New Cleistanthane Diterpenes and a New Isocoumarine from Cultures of the Basidiomycete Albatrellus confluens" Chemical and Pharmaceutical Bulletin, 2009, pp. 975-978, vol. 57, No. 9.
Registry—ACS on STN—CAS Registry No. 82710-10-9—Nov. 16, 1984.
International Search Report for PCT/JP2014/083519 dated Mar. 31, 2015.
Jiang, Wei et al., "Isolation and identification of two novel attractant compounds from Chinese cockroach (*Eupolyphaga sinensis* Walker) by combination of HSCCC, NMR and CD techniques" *Molecules*, 2013, pp. 11299-11310, vol. 18, No. 9.
Anderson et al. "Metabolites of the Higher Fungi. Part 21. 3-Methyl-3,4-dihydroisocoumarins and Related Compounds from the Ascomycete Family Xylariaceae," *J. Chem. Soc. Perkins Trans.* 1 (1983):2185-92.
Koshino et al. "Gamahonolides A, B, and Gamahorin, Novel Antifungal Compounds from Stromata of *Epicholoe typhina* on *Phleum pretense*," *Biosci. Biotech. Biochem.*, 1992, 56(7):1096-99.
Xu et al. "Polyketide derivatives of endophytic fungus *Pestalotiopsis* sp. Isolated from the Chinese mangrove plant *Rhizophora mucronata*," *Tetrahedron Letters*, 2011, 52:21-25.

* cited by examiner

COCKROACH ATTRACTION-AGGREGATION SUBSTANCE, COCKROACH AGGREGATION ATTRACTANT AND COCKROACH CONTROLLING AGENT

CROSS REFERENCE TO RELATED APPLICATIONS

This application is a U.S. National Phase Application of PCT International Application Number PCT/JP2014/083519, filed on Dec. 18, 2014, designating the United States of America and published in the English language, which is an International Application of and claims the benefit of priority to Japanese Patent Application No. 2013-269632, filed on Dec. 26, 2013. The disclosures of the above-referenced applications are hereby expressly incorporated by reference in their entireties.

TECHNICAL FIELD

The present invention relates to a cockroach attraction-aggregation substance, a cockroach attractant comprising the substance, and a cockroach controlling agent comprising the substance.

BACKGROUND ART

Cockroaches are common insect pests, infesting residential homes and industrial buildings and causing huge damage. Various elimination methods are used for cockroaches. However, their nests are very close to human activity, which limits the use of insecticides. In addition, cockroaches have a habit of hiding in narrow crevices and they are very fertile. Consequently, conventional insect traps or poisoned baits are not effective enough to eliminate cockroaches. Recent studies have revealed much about pheromones of cockroaches, and use of the pheromones for cockroach control has been investigated (Patent Literature 1, 2 and 3). Pheromones are chemicals secreted by organisms and are capable of acting on members of the same species. A small amount of pheromones is known to exhibit strong activity such as attraction activity.

Insect pheromones include sex pheromones and aggregation pheromones. Sex pheromones are pheromones that are secreted and released by an individual to attract the opposite sex. Aggregation pheromones are semiochemicals that trigger aggregation of members of the same species, excluding sex pheromones. That is, aggregation pheromones are chemicals that act on individuals regardless of males or females, also act on larvae, which have no reproductive ability.

The term aggregation pheromone was first used for the German cockroach. The German cockroach secretes pheromones from the end of the abdomen to mark a shelter. Pheromones are also present on the surface of the insect's body, allowing them to distinguish the individuals of the same species. The aggregation pheromones of the German cockroach include attractant pheromones such as 1-dimethylamino-2-methyl-2-propanol, which acts as a scent, and also include arrestant pheromones (arrestants), which are contact chemicals. Some of the components of the pheromones have been identified (Non-Patent Literature 1). The Blaberus cockroach (Blaberus craniifer) secretes aggregation pheromones from the mandibular gland in the head. Several substances with attraction activity, such as undecane, tetradecane and ethylcaproic acid, have been identified from the scent components collected with activated carbon.

Cockroach pheromones as described above are expected to serve as attractants in insect traps and poisoned baits, and thereby to increase the cockroach controlling effect. Conventionally known attractants, such as periplanones, bornyl acetate and terpenoids, lack long-lasting effect. In some cases, these conventional attractants may be turned into the opposite type of compounds serving as repellents. Thus the conventional attractants are unsatisfactory in practice. Sex pheromones are effective only for adults of the opposite sex. For these reasons, there was a growing demand for the identification and the use of cockroach aggregation pheromones that are effective for all individuals, regardless of larvae or adults, or females or males.

CITATION LIST

Patent Literature

Patent Literature 1: JP 6-24923 A
Patent Literature 2: JP 6-25279 A
Patent Literature 3: JP 2002-284610 A

Non-Patent Literature

Non-Patent Literature 1: Nogeikagaku no Jiten, edited by Akinori Suzuki and Soichi Arai, Asakura Publishing Co., Ltd., pp. 183-186.

SUMMARY OF INVENTION

Technical Problem

An object of the present invention is to provide a cockroach attraction-aggregation substance, and a cockroach aggregation attractant or a cockroach controlling agent comprising the substance.

Solution to Problem

The inventors conducted extensive studies to solve the above problems, and as a result found that the bodies and frass of American cockroaches contain cockroach attraction-aggregation substances. The inventors further conducted research and successfully identified the cockroach attraction-aggregation substances. The inventors continued further studies and completed the present invention.

That is, the present invention relates to the following.

(1) A compound serving as a cockroach attraction-aggregation substance, the compound being represented by general formula

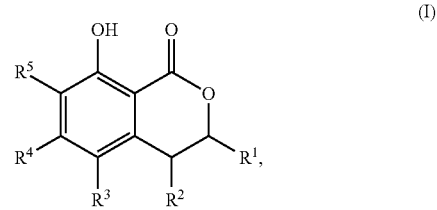

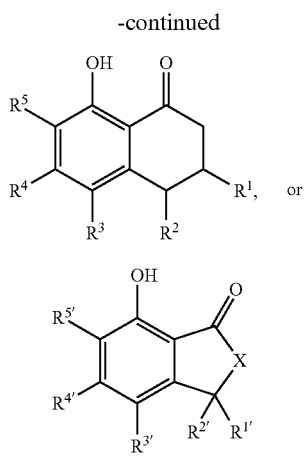

(wherein R¹ to R⁵ and R¹' to R⁵' are each independently a hydrogen atom, a halogen atom, a hydroxy group, a cyano group, a nitro group, a formyl group,
an optionally substituted $(C_1-C_6)$alkyl group,
an optionally substituted $(C_3-C_6)$cycloalkyl group,
an optionally substituted $(C_2-C_6)$alkenyl group,
an optionally substituted $(C_3-C_6)$cycloalkenyl group,
an optionally substituted $(C_2-C_6)$alkynyl group,
an optionally substituted $(C_1-C_6)$alkoxy group,
an optionally substituted $(C_3-C_6)$cycloalkoxy group,
an optionally substituted $(C_2-C_6)$alkenyloxy group,
an optionally substituted $(C_2-C_6)$alkynyloxy group,
an optionally substituted $(C_1-C_6)$alkoxy $(C_1-C_6)$alkyl group,
an optionally substituted $(C_3-C_6)$cycloalkyl $(C_1-C_6)$alkyl group,
an optionally substituted $(C_1-C_6)$alkoxyhalo $(C_1-C_6)$alkyl group,
an optionally substituted aryl group, or
an optionally substituted heteroaryl group;
X is a methylene group (—$CH_2$—) or an oxygen atom; and
R¹ and R², together with the carbon atoms to which they are attached, optionally form a 5-membered ring or a 6-membered ring), or
a salt thereof.

(2) The compound according to the above (1) or a salt thereof, wherein R¹ to R⁵ and R¹' to R⁵' are each independently a group selected from the group consisting of a hydrogen atom, a halogen atom, a hydroxy group, an optionally substituted $(C_1-C_6)$alkyl group, an optionally substituted $(C_3-C_6)$cycloalkyl group, an optionally substituted $(C_2-C_6)$alkenyl group, and an optionally substituted $(C_2-C_6)$alkynyl group.

(3) The compound according to the above (1) or (2) or a salt thereof, wherein R⁵ and R⁵' are a group selected from the group consisting of an optionally substituted $(C_1-C_6)$alkyl group, an optionally substituted $(C_3-C_6)$cycloalkyl group, an optionally substituted $(C_2-C_6)$alkenyl group, and an optionally substituted $(C_2-C_6)$alkynyl group.

(4) The compound according to any one of the above (1) to (3) or a salt thereof, wherein R¹ and R¹' are a group selected from the group consisting of an optionally substituted $(C_1-C_6)$alkyl group, an optionally substituted $(C_3-C_6)$cycloalkyl group, an optionally substituted $(C_2-C_6)$alkenyl group, and an optionally substituted $(C_2-C_6)$alkynyl group.

(5) The compound according to any one of the above (1) to (4) or a salt thereof, wherein R¹ and R⁵, and R¹' and R⁵' are a group selected from the group consisting of an optionally substituted $(C_1-C_6)$alkyl group, an optionally substituted $(C_3-C_6)$cycloalkyl group, an optionally substituted $(C_2-C_6)$alkenyl group, and an optionally substituted $(C_2-C_6)$alkynyl group.

(6) The compound according to any one of the above (3) to (5) or a salt thereof, wherein two of R², R³ and R⁴ are hydrogen atoms and the other is selected from the group consisting of an optionally substituted $(C_1-C_6)$alkyl group, an optionally substituted $(C_3-C_6)$cycloalkyl group, an optionally substituted $(C_2-C_6)$alkenyl group, and an optionally substituted $(C_2-C_6)$alkynyl group, or two of R²', R³' and R⁴' are hydrogen atoms and the other is selected from the group consisting of an optionally substituted $(C_1-C_6)$alkyl group, an optionally substituted $(C_3-C_6)$cycloalkyl group, an optionally substituted $(C_2-C_6)$alkenyl group, and an optionally substituted $(C_2-C_6)$alkynyl group.

(7) A compound serving as a cockroach attraction-aggregation substance, the compound being represented by formula

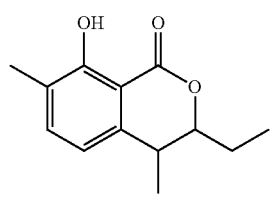

(I-1)

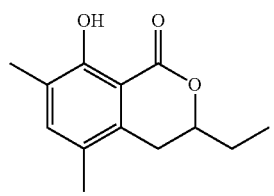

(I-2)

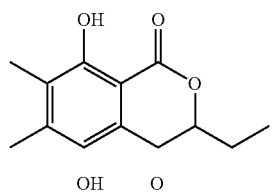

(I-3)

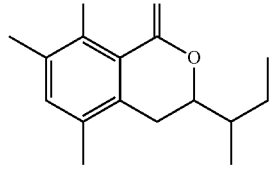

(I-4)

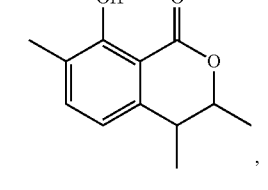

(I-5)

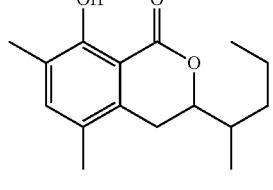

(I-6)

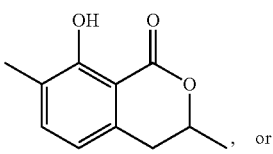

(I-7)

, or

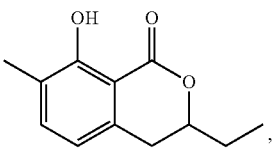

(I-8)

, or a salt thereof.

(8) A cockroach aggregation attractant comprising at least one or more of the compounds according to any one of the above (1) to (7) or a salt thereof.

(9) A cockroach controlling agent comprising at least one or more of the compounds according to any one of the above (1) to (7) or a salt thereof.

(10) Use of at least one or more of the compounds according to any one of the above (1) to (7) or a salt thereof, for attraction and aggregation of cockroaches or for control of cockroaches.

(11) A compound represented by formula

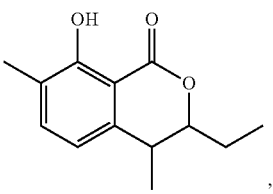

(I-1)

,

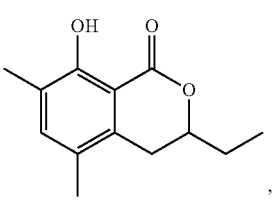

(I-2)

,

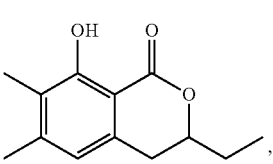

(I-3)

,

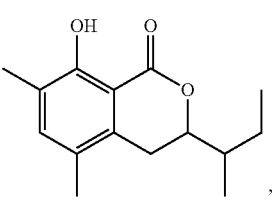

(I-4)

,

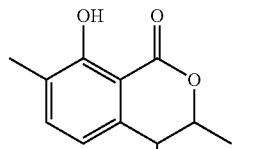

(I-5)

, or

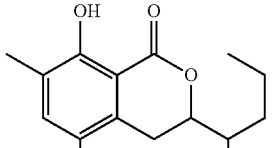

(I-6)

, or a salt thereof.

Advantageous Effects of Invention

The present invention provides a cockroach attraction-aggregation substance with excellent cockroach attraction-aggregation effect. The cockroach attraction-aggregation substance is used to provide a cockroach aggregation attractant and a cockroach controlling agent with high cockroach-attracting effect.

DESCRIPTION OF EMBODIMENTS

Figure 1:
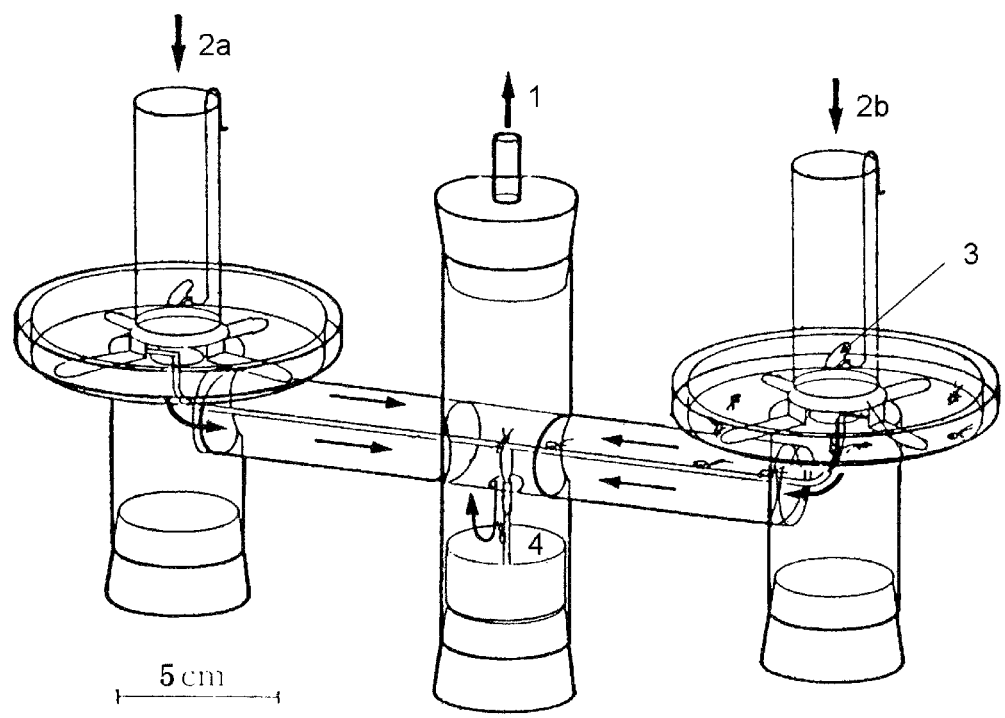
FIG. 1 is a schematic view of a linear track olfactometer used in a biological test for determining attraction-aggregation activity on cockroaches.

The term "cockroaches" herein means insects taxonomically classified into the Insecta class, the Blattaria order, excluding termites. Examples of the cockroaches include, but are not limited to, the German cockroach (*Blattella germanica*), the American cockroach (*Periplaneta americana*), the smokybrown cockroach (*Periplaneta fuliginosa*), and the Japanese cockroach (*Periplaneta japonica*).

An embodiment of the present invention relates to a cockroach attraction-aggregation substance.

The term "attraction-aggregation of cockroaches" includes attraction of cockroaches leading to their aggregation, regardless of adults or larvae, or males or females. The term "cockroach attraction-aggregation substance" herein refers to a substance that has attraction-aggregation activity on cockroaches, and hereinafter such a substance is also called "a cockroach attraction-aggregation compound" or "a cockroach aggregation pheromone".

The cockroach attraction-aggregation substance of the present invention is preferably a compound represented by general formula

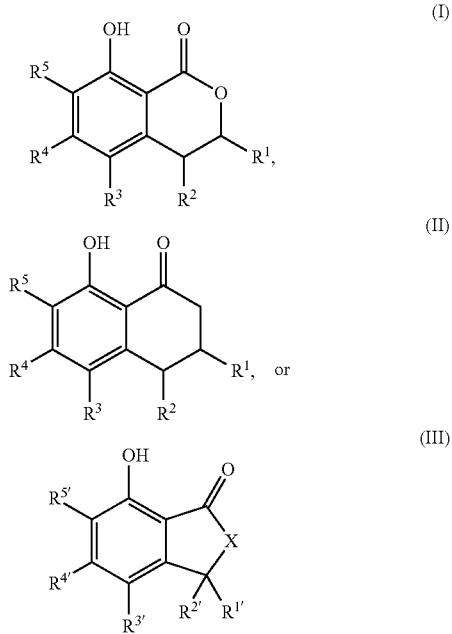

(wherein $R^1$ to $R^5$ and $R^{1'}$ to $R^{5'}$ are each independently a hydrogen atom, a halogen atom, a hydroxy group, a cyano group, a nitro group, a formyl group,
an optionally substituted $(C_1-C_6)$alkyl group,
an optionally substituted $(C_3-C_6)$cycloalkyl group,
an optionally substituted $(C_2-C_6)$alkenyl group,
an optionally substituted $(C_3-C_6)$cycloalkenyl group,
an optionally substituted $(C_2-C_6)$alkynyl group,
an optionally substituted $(C_1-C_6)$alkoxy group,
an optionally substituted $(C_2-C_6)$cycloalkoxy group,
an optionally substituted $(C_2-C_6)$alkenyloxy group,
an optionally substituted $(C_2-C_6)$alkynyloxy group,
an optionally substituted $(C_1-C_6)$alkoxy $(C_1-C_6)$alkyl group,
an optionally substituted $(C_2-C_6)$cycloalkyl $(C_1-C_6)$alkyl group,
an optionally substituted $(C_1-C_6)$alkoxyhalo $(C_1-C_6)$alkyl group,
an optionally substituted aryl group, or
an optionally substituted heteroaryl group;
$R^1$ and $R^2$, together with the carbon atoms to which they are attached, optionally form a 5-membered ring or a 6-membered ring; and
X is a methylene group ($-CH_2-$) or an oxygen atom), or a salt thereof.

Examples of the "$(C_1-C_6)$alkyl group" include linear or branched alkyl groups of 1 to 6 carbon atoms, such as a methyl group, an ethyl group, an n-propyl group, an isopropyl group, an n-butyl group, an isobutyl group, a sec-butyl group, a tert-butyl group, an n-pentyl group, an isopentyl group, a tert-pentyl group, a neopentyl group, a 2,3-dimethylpropyl group, a 1-ethylpropyl group, a 1-methylbutyl group, a 2-methylbutyl group, an n-hexyl group, an isohexyl group, a 2-hexyl group, a 3-hexyl group, a 2-methylpentyl group, a 3-methylpentyl group, a 1,1,2-trimethylpropyl group, and a 3,3-dimethylbutyl group.

Examples of the "$(C_3-C_6)$cycloalkyl group" include cyclic alkyl groups of 3 to 6 carbon atoms, such as a cyclopropyl group, a cyclobutyl group, a cyclopentyl group, and a cyclohexyl group.

Examples of the "$(C_2-C_6)$alkenyl group" include linear or branched alkenyl groups of 2 to 6 carbon atoms, such as a vinyl group, an allyl group, an isopropenyl group, a 1-butenyl group, a 2-butenyl group, a 2-methyl-2-propenyl group, a 1-methyl-2-propenyl group, a 2-methyl-1-propenyl group, a pentenyl group, a 1-hexenyl group, and a 3,3-dimethyl-1-butenyl group.

Examples of the "$(C_3-C_6)$cycloalkenyl group" include cyclic alkenyl groups of 3 to 6 carbon atoms, such as 2-cyclopenten-1-yl, 3-cyclopenten-1-yl, 2-cyclohexen-1-yl, and 3-cyclohexen-1-yl.

Examples of the "$(C_2-C_6)$alkynyl group" include linear or branched alkynyl groups of 2 to 6 carbon atoms, such as an ethynyl group, a 1-propynyl group, a 2-propynyl group, a 1-butynyl group, a 2-butynyl group, a 3-butynyl group, a 3-methyl-1-propynyl group, a 2-methyl-3-propynyl group, a pentynyl group, a 1-hexynyl group, a 3-methyl-1-butynyl group, and a 3,3-dimethyl-1-butynyl group.

Examples of the "$(C_1-C_6)$alkoxy group" include linear or branched alkoxy groups of 1 to 6 carbon atoms, such as a methoxy group, an ethoxy group, an n-propoxy group, an isopropoxy group, an n-butoxy group, a sec-butoxy group, a tert-butoxy group, an n-pentyloxy group, an isopentyloxy group, a tert-pentyloxy group, a neopentyloxy group, a 2,3-dimethylpropyloxy group, a 1-ethylpropyloxy group, a 1-methylbutyloxy group, an n-hexyloxy group, an isohexyloxy group, and a 1,1,2-trimethylpropyloxy group.

Examples of the "$(C_3-C_6)$cycloalkoxy group" include cyclic alkoxy groups of 3 to 6 carbon atoms, such as a cyclopropoxy group, a cyclobutoxy group, a cyclopentyloxy group, and a cyclohexyloxy group.

Examples of the "$(C_2-C_6)$alkenyloxy group" include linear or branched alkenyloxy groups of 2 to 6 carbon atoms, such as a propenyloxy group, a butenyloxy group, a pentenyloxy group, and a hexenyloxy group.

Examples of the "$(C_2-C_6)$alkynyloxy group" include linear or branched alkynyloxy groups of 2 to 6 carbon atoms, such as a propynyloxy group, a butynyloxy group, a pentynyloxy group, and a hexynyloxy group.

Examples of the "aryl group" include $(C_6-C_{14})$ aryl groups, such as a phenyl group, a 1-naphthyl group, a 2-naphthyl group, a 2-biphenylyl group, a 3-biphenylyl group, a 4-biphenylyl group, and 2-anthryl group.

Examples of the "heteroaryl group" include the groups derived from removal of a hydrogen atom from furan, imidazole, isothiazole, isoxazole, oxadiazole, oxazole, 1,2,3-oxadiazine, pyrazine, pyrazole, pyridazine, pyridine, pyrimidine, pyrroline, triazole, 1,3,4-thiadiazole, triazole, tetrazole, or the like.

The expressions "$(C_1-C_6)$", "$(C_2-C_6)$", "$(C_3-C_6)$", etc. indicate the ranges of the number of the carbon atoms in the substituents. The same definition is applied to a group formed by connecting the substituents. For example, the term "$(C_1-C_6)$alkoxy $(C_1-C_6)$alkyl group" refers to a group in which a linear or branched alkoxy group of 1 to 6 carbon atoms is bonded to a linear or branched alkyl group of 1 to 6 carbon atoms.

The salt in the present invention is exemplified by, but not limited to, acid addition salts, metal salts, ammonium salts, organic amine addition salts, and amino acid addition salts. Examples of the acid addition salts include, but are not limited to, inorganic acid salts such as hydrochlorides, sulfates, nitrates, and phosphates; and organic acid salts such as acetates, maleates, fumarates, oxalates, methanesulfonates, benzenesulfonates, p-toluenesulfonates, tartrates, and citrates. Examples of the metal salts include, but are not limited to, alkali metal salts such as sodium salts and potassium salts; alkaline earth metal salts such as calcium salts and magnesium salts; aluminum salts; and zinc salts. Examples of the ammonium salts include, but are not limited to, trimethylammonium salts, dimethylammonium salts, and monomethylammonium salts. Examples of the organic amine addition salts include, but are not limited to, addition salts such as trimethylamine salts, triethylamine salts, dicyclohexylamine salts, ethanolamine salts, diethanolamine salts, triethanolamine salts, procaine salts, N,N'-dibenzylethylenediamine salts, morpholine salts, and piperidine salts. Examples of the amino acid addition salts include, but are not limited to, addition salts such as lysine salts, glycine salts, and phenylalanine salts.

The 5-membered ring or the 6-membered ring formed by $R^1$ and $R^2$ together with the carbon atoms to which they are attached is not particularly limited and may be an alicyclic ring or an aromatic ring. Examples of the ring include cycloalkane rings, cycloalkene rings, aryl rings, and heteroaryl rings. Specific examples thereof include cyclopentane, cyclohexane, cyclopentene, cyclohexene, a benzene ring, and a pyridine ring.

The compound represented by any of general formulae (I) to (III) of the present invention and a salt thereof may have one or more asymmetric centers in the structural formula, and may include two or more optical isomers and diastereomers. The present invention encompasses all the optical isomers and mixtures thereof in any ratio.

In a preferred embodiment of the present invention, the cockroach attraction-aggregation substance is a compound represented by any of general formulae (I) to (III) wherein $R^1$ to $R^5$ and $R^{1'}$ to $R^{5'}$ are each independently a group selected from the group consisting of a hydrogen atom, a halogen atom, a hydroxy group, an optionally substituted $(C_1-C_6)$alkyl group, an optionally substituted $(C_3-C_6)$cycloalkyl group, an optionally substituted $(C_2-C_6)$alkenyl group, and an optionally substituted $(C_2-C_6)$alkynyl group, or a salt thereof. In this embodiment, $R^1$ and $R^2$, together with the carbon atoms to which they are attached, may form a 5-membered ring or a 6-membered ring.

In a more preferred embodiment of the present invention, the cockroach attraction-aggregation substance is a compound represented by any of general formulae (I) to (III) wherein $R^5$ and $R^{5'}$ are a group selected from the group consisting of an optionally substituted $(C_1-C_6)$alkyl group, an optionally substituted $(C_3-C_6)$cycloalkyl group, an optionally substituted $(C_2-C_6)$alkenyl group, and an optionally substituted $(C_2-C_6)$alkynyl group, or a salt thereof. In this embodiment, $R^1$ to $R^4$ and $R^{1'}$ to $R^{4'}$ in any of general formulae (I) to (III) may be as defined above. Preferably, in order to achieve high attraction-aggregation activity on cockroaches, $R^1$ to $R^4$ and $R^{1'}$ to $R^{4'}$ are each independently a group selected from the group consisting of a hydrogen atom, a halogen atom, a hydroxy group, an optionally substituted $(C_1-C_6)$alkyl group, an optionally substituted $(C_3-C_6)$cycloalkyl group, an optionally substituted $(C_2-C_6)$alkenyl group, and an optionally substituted $(C_2-C_6)$alkynyl group. In this embodiment, $R^1$ and $R^2$, together with the carbon atoms to which they are attached, may form a 5-membered ring or a 6-membered ring.

In another more preferred embodiment of the present invention, the cockroach attraction-aggregation substance is a compound represented by any of general formulae (I) to (III) wherein $R^1$ and $R^{1'}$ are a group selected from the group consisting of an optionally substituted $(C_1-C_6)$alkyl group, an optionally substituted $(C_3-C_6)$cycloalkyl group, an optionally substituted $(C_2-C_6)$alkenyl group, and an optionally substituted $(C_2-C_6)$alkynyl group, or a salt thereof. In this embodiment, $R^2$ to $R^5$ and $R^{2'}$ to $R^{5'}$ in any of general formulae (I) to (III) may be as defined above. Preferably, in order to achieve high attraction-aggregation activity on cockroaches, $R^2$ to $R^5$ and $R^{2'}$ to $R^{5'}$ are each independently a group selected from the group consisting of a hydrogen atom, a halogen atom, a hydroxy group, an optionally substituted $(C_1-C_6)$alkyl group, an optionally substituted $(C_3-C_6)$cycloalkyl group, an optionally substituted $(C_2-C_6)$alkenyl group, and an optionally substituted $(C_2-C_6)$alkynyl group.

In a further preferred embodiment of the present invention, the cockroach attraction-aggregation substance is a compound represented by any of general formulae (I) to (III) wherein $R^1$ and $R^5$, and $R^{1'}$ and $R^{5'}$ are a group selected from the group consisting of an optionally substituted $(C_1-C_6)$alkyl group, an optionally substituted $(C_3-C_6)$cycloalkyl group, an optionally substituted $(C_2-C_6)$alkenyl group, and an optionally substituted $(C_2-C_6)$alkynyl group, or a salt thereof. In this embodiment, $R^2$ to $R^4$ and $R^{2'}$ to $R^{4'}$ in any of general formulae (I) to (III) may be as defined above. Preferably, in order to achieve high attraction-aggregation activity on cockroaches, $R^2$ to $R^4$ and $R^{2'}$ to $R^{4'}$ are each independently a group selected from the group consisting of a hydrogen atom, a halogen atom, a hydroxy group, an optionally substituted $(C_1-C_6)$alkyl group, an optionally substituted $(C_3-C_6)$cycloalkyl group, an optionally substituted $(C_2-C_6)$alkenyl group, and an optionally substituted $(C_2-C_6)$alkynyl group. In this embodiment, $R^1$ and $R^2$, together with the carbon atoms to which they are attached, may form a 5-membered ring or a 6-membered ring.

The term "optionally substituted" herein includes the cases where a hydrogen atom is replaced by an atom or group other than hydrogen. Examples of the atom or group other than hydrogen include, but are not limited to, a halogen atom (such as a fluorine atom, a chlorine atom, a bromine atom, and an iodine atom), a nitro group, a cyano group, a hydroxy group, a $(C_1-C_6)$alkyl group, a $(C_3-C_6)$cycloalkyl group, a $(C_2-C_6)$alkenyl group, a $(C_3-C_6)$cycloalkenyl group, a $(C_2-C_6)$alkynyl group, a $(C_1-C_6)$alkoxy group, a $(C_3-C_6)$cycloalkoxy group, a $(C_2-C_6)$alkenyloxy group, a $(C_2-C_6)$alkynyloxy group, a $(C_1-C_6)$alkylthio group, a $(C_3$-

$C_6$)cycloalkylthio group, a ($C_2$-$C_6$)alkenylthio group, a ($C_2$-$C_6$)alkynylthio group, a ($C_1$-$C_6$)alkylsulfinyl group, a ($C_3$-$C_6$)cycloalkylsulfinyl group, a ($C_2$-$C_6$)alkenylsulfinyl group, a ($C_2$-$C_6$)alkynylsulfinyl group, a ($C_1$-$C_6$)alkylsulfonyl group, a ($C_3$-$C_6$)cycloalkylsulfonyl group, a ($C_2$-$C_6$) alkenylsulfonyl group, a ($C_1$-$C_6$)alkoxy ($C_1$-$C_6$)alkyl group, a ($C_3$-$C_6$)cycloalkyl ($C_1$-$C_6$)alkyl group, a ($C_1$-$C_6$)alkoxyhalo ($C_1$-$C_6$)alkyl group, an aryl group, and a heteroaryl group. Specific examples of these groups include those described above.

The number of substitutions with these substituents on any of the "optionally substituted" groups is preferably about 1 to 6. When more than one substituent is present in the group, the substituents may be the same or different.

In a particularly preferred embodiment of the present invention, the cockroach attraction-aggregation substance is a compound represented by formula

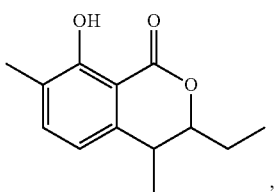
(I-1)

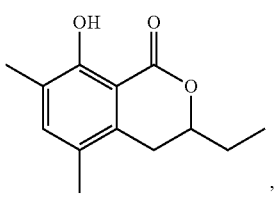
(I-2)

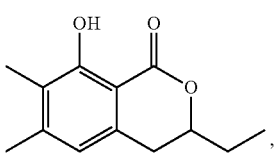
(I-3)

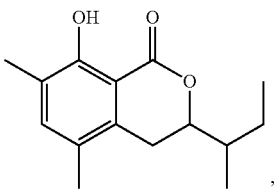
(I-4)

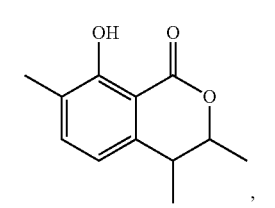
(I-5)

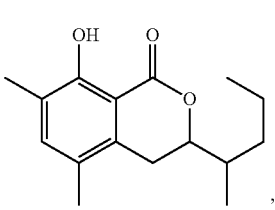
(I-6)

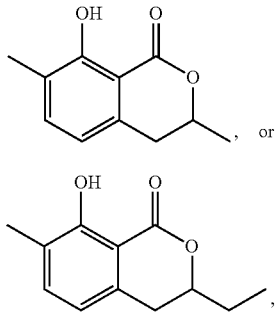
(I-7)

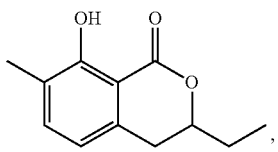
(I-8)

or
a salt thereof.

The production method of the cockroach attraction-aggregation substance of the present invention is not particularly limited, and the cockroach attraction-aggregation substance may be produced by chemical synthesis or extraction from the bodies or frass of cockroaches. Alternatively, the cockroach attraction-aggregation substance may be produced by chemical modification of a substance extracted from the bodies or frass of cockroaches. The bodies or frass of cockroaches are not particularly limited, but are preferably those derived from American cockroaches.

In another embodiment of the present invention, the cockroach attraction-aggregation substance may be a compound represented by general formula

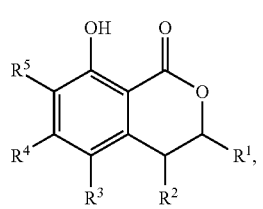
(I)

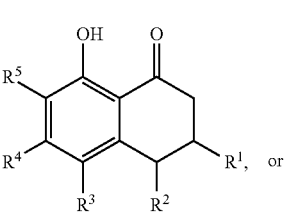
(II)

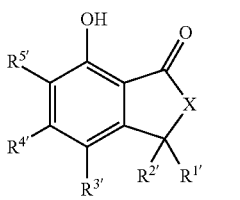
(III)

(wherein $R^1$ to $R^5$ and $R^{1'}$ to $R^{5'}$ are each independently a hydrogen atom, a halogen atom, a hydroxy group, a cyano group, a nitro group, a formyl group,
an optionally substituted ($C_1$-$C_6$)alkyl group,
an optionally substituted ($C_3$-$C_6$)cycloalkyl group,
an optionally substituted ($C_2$-$C_6$)alkenyl group,
an optionally substituted ($C_3$-$C_6$)cycloalkenyl group,
an optionally substituted ($C_2$-$C_6$)alkynyl group,
an optionally substituted ($C_1$-$C_6$)alkoxy group, an optionally substituted ($C_3$-$C_6$)cycloalkoxy group,
an optionally substituted ($C_2$-$C_6$)alkenyloxy group,
an optionally substituted ($C_2$-$C_6$)alkynyloxy group,
an optionally substituted ($C_1$-$C_6$)alkoxy ($C_1$-$C_6$)alkyl group,
an optionally substituted ($C_3$-$C_6$)cycloalkyl ($C_1$-$C_6$)alkyl group,
an optionally substituted ($C_1$-$C_6$)alkoxyhalo ($C_1$-$C_6$)alkyl group,
an optionally substituted aryl group, or
an optionally substituted heteroaryl group;
$R^1$ and $R^2$ may form a ring together with the carbon atoms to which they are attached;
any two of $R^3$ to $R^5$ may form a ring together with the carbon atoms to which they are attached;
any two of $R^{3'}$ to $R^{5'}$ may form a ring together with the carbon atoms to which they are attached; and
X is a methylene group (—$CH_2$—) or an oxygen atom, or a salt thereof.

The ring formed by $R^1$ and $R^2$ together with the carbon atoms to which they are attached, the ring formed by any two of $R^3$ to $R^5$ together with the carbon atoms to which they are attached, and the ring formed by any two of $R^{3'}$ to $R^{5'}$ together with the carbon atoms to which they are attached are not particularly limited, and may be an alicyclic ring or an aromatic ring. Examples of the rings include cycloalkane rings, cycloalkene rings, heteroalkyl rings, aryl rings, and heteroaryl rings. Specific examples thereof include cyclopentane, cyclohexane, cyclopentene, cyclohexene, a dihydrofuran ring, a dioxolane ring, a benzene ring, a naphthalene ring, and a pyridine ring. The number of carbon atoms in the rings is not particularly limited, but is preferably 3 to 15.

In an embodiment of the present invention, the compound represented by any of general formulae (I) to (III) may exclude the case where $R^1$ and $R^{1'}$ are a halogen atom.

The production method of the cockroach attraction-aggregation substance of the present invention will be described in detail below.

The synthetic method of the compound represented by general formula (I) and a salt thereof will be described below.

The synthetic method of the compound represented by general formula (I) or a salt thereof is not particularly limited, and the compound or a salt thereof can be synthesized by an appropriately selected known technique in the art (for example, the methods described in Synlett, 2006, No. 6, 873-876 and Biosci. Biotechnol. Biochem., 74(8), 1635-1640).

Specifically, the starting material to produce the compound or a salt thereof may be, for example, a 2-methoxy-N,N-dialkylbenzamide derivative of the formula:

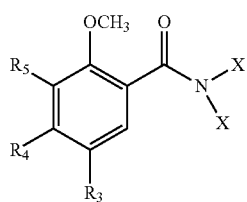

(wherein X is a lower alkyl group; and $R^3$ to $R^5$ are the substituents as described above) or a 2-methoxy-N-alkylbenzamide derivative of the formula:

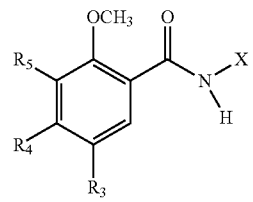

(wherein X is a lower alkyl group; and $R^3$ to $R^5$ are the substituents as described above).

The "lower alkyl group" is not particularly limited and may be, for example, a linear or branched alkyl group of 1 to 10 carbon atoms.

The production method of the compound represented by general formula (I) and a salt thereof by extraction from the bodies or frass of cockroaches will be described below.

In an embodiment of the present invention, the production method of the compound of general formula (I) by extraction from the bodies or frass of cockroaches may comprise (A) an extraction step using an organic solvent and (B) a separation and purification step by column chromatography.

The organic solvent used in step (A) may be a polar organic solvent or a nonpolar organic solvent. Examples of the polar organic solvent include alcohols such as methanol, ethanol, propanol, isopropanol, butanol, amyl alcohol, hexanol, heptanol, and octanol; ketones such as methyl ethyl ketone, methyl isobutyl ketone, acetone, acetylacetone, and cyclohexanone; nitriles such as acetonitrile, propionitrile, and benzonitrile; and organic acids such as formic acid, acetic acid, propionic acid, butyric acid, and valeric acid. Examples of the nonpolar organic solvent include saturated hydrocarbons such as n-pentane, n-hexane, n-heptane, n-octane, n-nonane, n-decane, 2-methylhexane, 3-methylhexane, 2,2,4-trimethylpentane, cyclopentane, cyclohexane, and cycloheptane; halogenated alkyls such as chloromethane, dichloromethane, trichloromethane, carbon tetrachloride, chloroethane, dichloroethane, and trichloroethane; ethers such as diethyl ether, diisopropyl ether, di-n-butyl ether, t-butyl methyl ether, tetrahydrofuran, anisole, and veratrole; esters such as methyl acetate, ethyl acetate, ethyl propionate, ethyl benzoate, and dimethyl phthalate; and lactones such as γ-butyrolactone. These solvents can be used singly or in combination of two or more of them. When two or more of the solvents are used in combination, the mixing ratio is not particularly limited, and can be appropriately selected depending on the types of solvents to be combined or the type of compound to be extracted. Preferred in the present invention are alcohols, saturated hydrocarbons, and/or halogenated alkyls.

Of the above organic solvents, preferred are n-hexane, dichloromethane, and a mixed solvent of methanol/dichloromethane. The mixing ratio of the mixed solvent of methanol/dichloromethane may be any ratio, but is preferably 1/99 to 5/95 (v/v).

Step (A) preferably comprises the following steps (1) and (2):
step (1) of washing the bodies and/or frass of cockroaches with n-hexane, then subjecting the bodies and/or frass to extraction with a mixed solvent of methanol/dichloromethane, and removing the solvent to give an extract; and
step (2) of dissolving the extract of step (1) in dichloromethane, then adding a sodium carbonate aqueous solution to perform liquid-liquid partition, separating the dichloromethane layer, and removing the solvent to give a dichloromethane extract.

In step (1), the washing with n-hexane and the extraction with a methanol/dichloromethane solution are not limited to particular methods. Preferably, the extraction is solid-liquid extraction. The solid-liquid extraction may be conducted in a conventional manner. The solid-liquid extraction can be performed as follows. For example, a solvent (n-hexane or a methanol/dichloromethane solution) is added to a solid sample (the bodies and/or frass of cockroaches), and then the mixture is separated into the solid sample and the solvent by suction filtration or gravity filtration. The solvent in the methanol/dichloromethane extract can be removed by, for example, distillation under reduced pressure with a rotary evaporator.

In step (2), the amount of a 1 N sodium carbonate aqueous solution to be added to the solution of the extract of step (1) in dichloromethane is not particularly limited, but typically, the ratio of the 1 N sodium carbonate aqueous solution to the dichloromethane solution is 1/1 (v/v). After addition of the 1 N sodium carbonate aqueous solution, liquid-liquid partition can be conducted in a conventional manner. The dichloromethane layer and the aqueous sodium carbonate layer are separated in a conventional manner, and the solvent in the dichloromethane layer is removed to give an extract. The removal of the solvent in the dichloromethane layer may be performed by any method, for example, distillation under reduced pressure using a rotary evaporator.

Purification in step (B) may be conducted by a combination of normal-phase silica gel chromatography, reversed-phase silica gel chromatography, and/or ion exchange resin column chromatography.

The solvent used in step (B) may be a protic solvent or a non-protic solvent. Examples of the protic solvent include water; alcohols such as methanol, ethanol, propanol, isopropanol, butanol, amyl alcohol, hexanol, heptanol, and octanol; and organic acids such as formic acid, acetic acid, propionic acid, butyric acid, and valeric acid. Examples of the non-protic solvent include saturated hydrocarbons such as n-pentane, n-hexane, n-heptane, n-octane, n-nonane, n-decane, 2-methylhexane, 3-methylhexane, 2,2,4-trimethylpentane, cyclopentane, cyclohexane, and cycloheptane; halogenated alkyls such as chloromethane, dichloromethane, trichloromethane, carbon tetrachloride, chloroethane, dichloroethane, and trichloroethane; ethers such as diethyl ether, diisopropyl ether, di-n-butyl ether, t-butyl methyl ether, tetrahydrofuran, anisole, and veratrole; ketones such as methyl ethyl ketone, methyl isobutyl ketone, acetone, acetylacetone, and cyclohexanone; esters such as methyl acetate, ethyl acetate, ethyl propionate, ethyl benzoate, and dimethyl phthalate; nitriles such as acetonitrile, propionitrile, and benzonitrile; and lactones such as γ-butyrolactone. These solvents can be used singly or in combination of two or more of them. When two or more solvents are used in combination, the mixing ratio is not particularly limited, and can be appropriately selected depending on the types of solvents to be combined or the type of compound to be extracted. Preferred in the present invention are water, alcohols, saturated hydrocarbons, esters, and/or nitriles.

In a preferred embodiment of the present invention, step (B) comprises the following steps (3) to (8):

step (3) of sequentially fractionating the extract of step (2) by normal-phase silica gel column chromatography using a mixed solvent of dichloromethane/n-hexane and then using a mixed solvent of ethyl acetate/n-hexane as development solvents, and removing the solvent from the ethyl acetate/n-hexane fraction to give an ethyl acetate/n-hexane eluate;

step (4) of dissolving the eluate or extract of step (3) in acetone, then adding activated carbon to the solution and allowing to stand, removing the activated carbon to give an acetone fraction, and removing the solvent from the acetone fraction to give an acetone eluate;

step (5) of fractionating the acetone eluate of step (4) by ion exchange resin column chromatography using a mobile phase of a mixed solvent of methanol/water to give a methanol/water eluate;

step (6) of fractionating the eluate of step (5) by normal-phase silica gel column chromatography using a mixed solvent of ethyl acetate/n-hexane as a development solvent to give an ethyl acetate/n-hexane fraction, and removing the solvent from the fraction to give an ethyl acetate/n-hexane eluate;

step (7) of fractionating the eluate of step (6) by normal-phase HPLC using a mobile phase of ethyl acetate/n-hexane to give a fraction, and removing the solvent from the fraction to give an eluate;

step (8) of fractionating the eluate of step (7) by reversed-phase HPLC using a mobile phase of methanol to give an eluate;

step (9) of fractionating the eluate of step (8) by reversed-phase HPLC using a mobile phase of a mixed solvent of isopropanol/methanol to give an eluate; and step (10) of fractionating the eluate of step (9) by normal-phase HPLC using a mobile phase of a mixed solvent of methyl acetate/n-hexane to give a fraction, and removing the solvent from the fraction.

Preferably, the fractions obtained in each of steps (3) to (10) are assessed by a biological test using the linear track olfactometer described later to determine the attraction-aggregation activity on cockroaches, and fractions with high activity are selected to be subjected to the subsequent steps and/or operations.

In step (3), the normal-phase silica gel chromatography is preferably open column chromatography on a column filled with silica gel. The fractionation of the extract on an open column filled with silica gel can be performed in a conventional manner. For example, the fractionation can be conducted by loading the extract on silica gel packed in a column, and passing a solvent through the column under reduced pressure. Removal of the solvent from the resulting eluate can be done by any method, for example, distillation under reduced pressure using a rotary evaporator.

In step (3), the mixing ratio of the mixed solvent of dichloromethane/n-hexane may be any ratio, but is preferably 5/95 to 40/60 (v/v). In order to improve the purification efficiency, the mixing ratio is more preferably 5/95 to 35/65 (v/v). The mixing ratio of the mixed solvent of ethyl acetate/n-hexane may be any ratio, but is preferably 0.5/99.5 to 15/85 (v/v). In order to improve the purification efficiency, the mixing ratio is more preferably 0.5/99.5 to 10/90 (v/v).

In step (4), the acetone fraction may be obtained as follows. For example, the solvent is removed from the ethyl acetate/n-hexane fraction obtained in step (3), the resulting solid is dissolved in acetone, then activated carbon is added to the solution, the mixture is allowed to stand for a certain period of time, and the activated carbon is removed to give the acetone fraction. The amount of acetone to be used to dissolve the solid obtained from the ethyl acetate/n-hexane fraction may be, for example, about 5 to about 100 mL relative to 1 g of the solid, and is preferably about 30 to about 80 mL relative to 1 g of the solid. The amount of the activated carbon to be added to the acetone solution may be about 1 to about 5 times the weight of the solid, and is preferably about 2 to about 4 times the weight of the solid. The activated carbon may be removed by, for example, filtration.

In step (5), the fractionation of the eluate on an open column filled with an ion exchange resin can be performed in a conventional manner. For example, the fractionation can be conducted by re-dissolving the dried eluate in a solvent such as methanol, then mixing the solution with an ion exchange resin to prepare a suspension, loading the suspension on a column, and sequentially passing solvents through the column. The removal of the solvents in the eluate or the concentration of the eluate can be done by any method. For example, the solvents may be removed by distillation under reduced pressure with a rotary evaporator, or the eluate may be concentrated under reduced pressure. The ion exchange resin is preferably porous polymer beads (for example, CHP20P produced by Mitsubishi Chemical Corporation).

In step (5), the mixing ratio of the mixed solvent of methanol/water may be any ratio, but is preferably 0/100 to 100/0 (v/v). In order to improve the purification efficiency, the ratio is more preferably 0/100 to 99/1 (v/v).

In a preferred embodiment of step (5), the eluate obtained in step (4) is sequentially fractionated on an open column filled with an ion exchange resin with mobile phases of methanol/water (0/100 (v/v)), methanol/water (85/15 (v/v)), and methanol/water (95/5 (v/v)).

In step (6), the normal-phase silica gel chromatography is preferably open column chromatography on a column filled with silica gel. The fractionation of the extract on an open column filled with silica gel can be performed in a conventional manner. For example, the fractionation can be conducted by loading the eluate on silica gel packed in a column, and passing the solvent through the column. The removal of the solvent from the eluate can be done by any method, for example, distillation under reduced pressure with a rotary evaporator.

In step (6), the mixing ratio of the mixed solvent of ethyl acetate/n-hexane may be any ratio, but is preferably 1/99 to 10/90 (v/v). In order to improve the purification efficiency, the ratio is more preferably 1/99 to 8/92 (v/v).

In step (7), the mixing ratio of the mixed solvent of ethyl acetate/n-hexane may be any ratio, but is preferably 1/99 to 10/90 (v/v). In order to improve the purification efficiency, the ratio is more preferably 1/99 to 8/92 (v/v).

In step (7), the purification by normal-phase HPLC can be performed as follows. For example, the eluate obtained in step (6) can be purified on an HPLC instrument equipped with a normal-phase column by passing the eluate through the column using a mobile phase of a mixed solution of ethyl acetate/n-hexane. The normal-phase column may be a silica gel column (COSMOSIL 5SL-II produced by Nacalai Tesque, 4.6 mm diameter×150 mm). The details of the purification conditions will be described in Examples described later.

In step (8), the mobile phase may be methanol or acetonitrile, and a mixed solvent of methanol/acetonitrile can also be used. The mixing ratio of the mixed solvent may be any ratio. A preferred mobile phase is 100% methanol.

In step (8), the purification by reversed-phase HPLC can be performed as follows. For example, the eluate separated in step (7) can be purified on an HPLC instrument equipped with a reversed-phase column by passing the eluate through the column using a mobile phase of 100% methanol. The reversed-phase column may be an ODS column (COSMOSIL 5AR-II produced by Nacalai Tesque, 4.6 mm diameter× 150 mm). The details of the purification conditions will be described in Examples described later.

In step (9), the mixing ratio of the mixed solvent of isopropanol/methanol may be any ratio, but is preferably 20/80 to 80/20 (v/v). In order to improve the purification efficiency, the ratio is more preferably 35/65 to 65/35 (v/v).

In step (9), the purification by HPLC can be performed as follows. For example, the eluate obtained in step (8) can be purified on an HPLC instrument equipped with a reversed-phase column by passing the eluate through the column using a mobile phase of an isopropanol/methanol (50/50 (v/v)) solution. The reversed-phase column may be, for example, a COSMOSIL ICNAP column (produced by Nacalai Tesque, 4.6 mm diameter×150 mm). The details of the purification conditions will be described in Examples described later.

In step (10), the mixing ratio of the mixed solvent of ethyl acetate/n-hexane may be any ratio, but is preferably 0.1/99.9 to 10/90 (v/v). In order to improve the purification efficiency, the ratio is more preferably 0.1/99.9 to 5/95 (v/v).

In step (10), the purification by HPLC can be performed as follows. For example, the eluate obtained in step (9) can be purified on an HPLC instrument equipped with a normal-phase column by passing the eluate through the column using a mobile phase of an ethyl acetate/n-hexane (0.5/99.5 (v/v)) solution. The normal-phase column may be a silica gel column (COSMOSIL 5SL-II, produced by Nacalai Tesque, 4.6 mm diameter×150 mm). The details of the purification conditions are described in Examples described later. The removal of the solvent may be done by any method, for example, distillation under reduced pressure with a rotary evaporator.

The method for determining the activity of the cockroach attraction-aggregation substance is not particularly limited herein, and the activity may be determined by, for example, a biological test using a linear track olfactometer (FIG. 1).

An olfactometer (linear track olfactometer) is typically an instrument used to conduct bioassays to observe the response of insects to volatiles. The instrument has a bifurcation at which air flow containing an attractant substance attracts the insect subjects (see, e.g., J. Jpn. For. Soc., 89(2), 2007, "An Olfactometer Testing the Olfactory Response of the Japanese Horntail *Urocerus japonicus* to Volatiles.", 135-137, and Nogyo Kankyo Kenkyu Sosho, Vol. 17, "Nogyo Seitaikei no Hozen ni Muketa Seibutsu Kino no Katsuyo", 108-134).

A biological test with a linear track olfactometer will be specifically described below. In FIG. 1, air suction from the top 1 of the central tube allows air to enter from the tops (2a and 2b) of the right and left tubes, thereby air flows are generated from the both sides, flowing through the horizontal tube toward the top of the central tube. The left tube is the control side, and the right tube is the sample side. A sample is applied to a metal disk 3 hanged from the top of the tube as shown in FIG. 1. Insect subjects (7 to 10 day-old larvae) are placed at the bottom 4 of the central tube. Air is then slowly suctioned from the top of the central tube with a pump (2.5 L/min). The insect subjects are allowed to freely move for 5 minutes at 25±1° C. at a relative humidity of 40 to 60% in total darkness. The numbers of the insect subjects that have moved to the control side and to the sample side are counted. The excess proportion index (EPI) is calculated by the following equation:

$$EPI=(NS-NC)/(NS+NC)$$

(where NS is the number of the insect subjects that have moved to the sample side; and NC is the number of the insect subjects that have moved to the control side).

An EPI closer to 1 indicates higher attraction-aggregation activity on cockroaches.

Another embodiment of the present invention relates to a cockroach controlling agent or a cockroach aggregation attractant comprising the compound represented by any of general formulae (I) to (III).

The amount of the compound represented by any of general formulae (I) to (III) or a salt thereof contained in the cockroach controlling agent or the cockroach aggregation attractant of the present invention is not particularly limited as long as the cockroach attraction-aggregation effect is exhibited. The amount of the compound or a salt thereof can be appropriately selected depending on the dosage form, the application, and the place to which the controlling agent or the attractant is to be applied. For example, the compound represented by any of general formulae (I) to (III) or a salt thereof may be contained in the cockroach controlling agent typically at a concentration of $2.0 \times 10^{-7}$ ppm to 1 ppm ($2.0 \times 10^{-11}$ to $1.0 \times 10^{-4}$% by weight), preferably $4.0 \times 10^{-6}$ ppm to 0.5 ppm ($4.0 \times 10^{-10}$ to $5.0 \times 10^{-5}$% by weight), relative to the total amount of the cockroach controlling agent.

Still another embodiment of the present invention relates to a cockroach controlling agent comprising the extract or the eluate obtained in any of the above steps (1) to (9). As with the above-described cockroach attraction-aggregation substance, the extracts or the eluates obtained in steps (1) to (9) (hereinafter, the extract obtained in step (1) is also called a crude extract) also have excellent cockroach attraction-aggregation effect, and can serve as cockroach attraction-aggregation substances. Of the extracts or the eluates obtained in steps (1) to (9), preferred is the extract obtained in step (1), which exhibits high cockroach attraction-aggregation effect and can be prepared by a simple operation.

The amount of the extract of step (1) contained in the cockroach controlling agent of the present invention is not particularly limited as long as the cockroach attraction-aggregation effect is exhibited. The amount of the extract can be appropriately selected depending on the dosage form, the application, and the place to which the controlling agent is to be applied. The amount of the extract is typically 3 ppm to 200,000 ppm ($3.0 \times 10^{-4}$ to 20% by weight) and preferably 50 ppm to 20,000 ppm ($5.0 \times 10^{-3}$ to 2% by weight).

In a preferred embodiment of the present invention, the cockroach attraction-aggregation substance of the present invention may be blended into, for example, a poisoned bait containing an insecticide, or in a bait for sticky insect traps. The cockroach attraction-aggregation substance can also be added, as needed, to various types of cockroach controlling agents in the form of, for example, solid agents (e.g., powders and granules), aerosols, liquids, sheets, etc. to improve the controlling effect. If needed, various types of additives may be added to the cockroach controlling agent or the cockroach aggregation attractant of the present invention in accordance with the general knowledge in the art.

Examples of the insecticide include, but are not limited to, pyrethroids such as pyrethrin, allethrin, flumethrin, resmethrin, phenothrin, permethrin, phthalthrin, imiprothrin, cyphenothrin, permethrin, fenvalerate, ethofenprox, prallethrin, fenfluthrin, and transfluthrin; organophosphorus agents such as fenitrothion, trichlorfon, dichlorvos, pyridaphenthion, diazinon, and fenthion; carbamates such as carbaryl, 2-(1-methylpropyl)phenyl methylcarbamate (BPMC), propoxur, and cevine; oxadiazole insecticides such as metoxadiazone; hydrazone insecticides such as hydramethylnon; phenylpyrazole insecticides such as fipronil; and boric acid and borates. These insecticides may be microencapsulated or complexed with a cyclodextrin. Examples of a carrier used to prepare the poisoned baits include various types of mineral powders such as silicic acid, kaolin, and talc; various types of plant powders such as wood powder, corn powder, wheat flour, and starch; other substances such as molasses, skim milk, and fish powder; and excipients and binders such as abion. Examples of a substrate used to prepare the sticky insect traps include natural rubber adhesives; and synthetic rubber adhesives containing polybutene or polyisobutene as a main component and containing rosin or paraffin wax for improving the adhesive power. Optionally, auxiliary components such as fragrances, deodorizers, antiseptics, stabilizers, and solvents can be added as needed to provide a multi-purpose composition with excellent efficacy.

The cockroach controlling agent or the cockroach aggregation attractant produced as above are placed in the area where cockroaches may crawl across, such as the kitchen, warehouses, and behind the refrigerator. The cockroach controlling agent or aggregation attractant then exhibits high attraction-aggregation effect and/or high controlling effect on German cockroaches, smokybrown cockroaches, and American cockroaches. The form of the cockroach controlling agent or the cockroach aggregation attractant of the present invention is not particularly limited, and may be a liquid or solid.

Examples of a carrier used to prepare the liquid agent include, but are not limited to, water; alcohols such as methanol and ethanol; ketones such as acetone and methyl ethyl ketone; ethers such as tetrahydrofuran and dioxane; aliphatic hydrocarbons such as hexane, kerosene, paraffin, and petroleum benzene; aromatic hydrocarbons such as benzene and toluene; esters such as ethyl acetate; and halogenated hydrocarbons such as dichloroethane. The liquid agent may further contain a common additive, such as a film-forming agent, an emulsifier, a dispersant, a spreader, a wetting agent, a stabilizer, and a propellant. The liquid agent may be in the form of, for example, a liquid to be applied on a surface, an adhesive, an emulsion, a dispersant, a suspension, a lotion, a paste, a cream, a spray, and an aerosol.

Examples of the additive further include cellulose derivatives such as nitrocellulose, acetyl cellulose, acetyl butyryl cellulose, methyl cellulose, and carboxymethyl cellulose; vinyl resins such as vinyl acetate resins; film forming agents such as alkyd resins, urea resins, epoxy resins, polyester resins, urethane resins, silicone resins, acrylic resins, chlorinated rubbers, and polyvinyl alcohols; soaps; polyoxyethylene fatty alcohol ethers such as polyoxyethylene oleyl ether; polyoxyethylene alkylaryl ethers such as polyoxyethylene nonylphenyl ether; surfactants such as polyoxyethylene fatty acid esters, fatty acid glycerides, sorbitan fatty acid esters, sulfuric acid esters of higher alcohols, and alkyl aryl sulfonates including sodium dodecylbenzenesulfonate; propellants such as liquefied petroleum gas, dimethyl ether, fluorocarbons, and liquefied carbon dioxide gas; and casein, gelatin, and alginic acid.

Examples of a carrier used to prepare the solid agent include mineral powders such as silicic acid, kaolin, activated carbon, bentonite, zeolite, diatomaceous earth, talc, clay, calcium carbonate, and ceramic powders; plant powders such as wood powder, soybean powder, wheat flour, and starch; inclusion compounds such as cyclodextrins; fiber carriers such as pulp, linter, and rayon; and beads and foams made from cellulose and regenerated cellulose. The solid agent can be prepared as a sublimable solid by melt-blending or grinder-blending of the attractant active substance with a sublimable carrier such as tricyclodecane, cyclododecane, 2,4,6-triisopropyl-1,3,5-trioxane and trim-ethylenenorbornene, or a sublimable insecticide such as p-dichlorobenzene, naphthalene and camphor, etc., and then shaped into a solid form.

The compound represented by any of general formulae (I) to (III) or a salt thereof can be formulated into microcapsules by, for example, spray drying using polyvinyl alcohol, carboxymethyl cellulose, etc.; in-liquid curing using gelatin, polyvinyl alcohol, alginic acid, etc.; or coacervation. Alternatively, the compound or a salt thereof can be formulated into a gel by using a gelling agent such as benzylidene-D-sorbitol and carrageenan. In addition, the cockroach attraction-aggregation substance of the present invention can be combined with, for example, a dog and cat repellent, a bird repellent, a snake repellent, an insecticide, a miticide, an effect enhancer, an antioxidant, a rodent controlling agent, a rodent repellent, an insect growth regulator, a bait substance; another attractant active substance, such as ammonia, alkylamines (e.g., methylamine, dimethylamine, trimethylamine, diethylamine, isobutylamine, or isoamylamine), amino alcohols (e.g., 2-dimethylaminoethanol, 1-dimethylamino-2-methyl-2-propanol, or 2-dimethylamino-2-methyl-1-propanol), periplanones, bornyl acetate, and terpenoids; or an antiseptic, an antifungal agent, a preservative, a flavoring agent, a coloring agent, an agent for preventing accidental ingestion, or the like.

Another embodiment of the present invention relates to a compound represented by formula

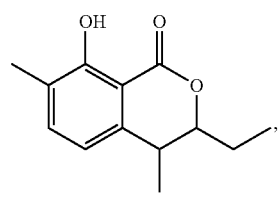
(I-1)

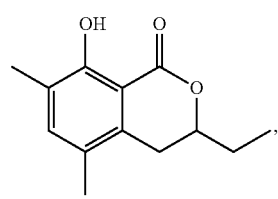
(I-2)

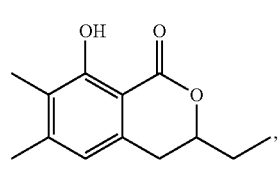
(I-3)

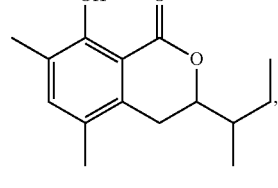
(I-4)

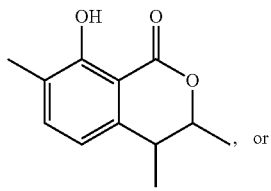
(I-5)

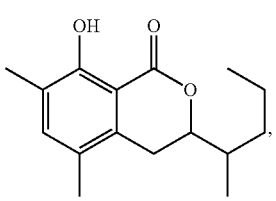
(I-6)

or
a salt thereof

The compound represented by any of formulae (I-1) to (I-6) or a salt thereof can be produced by the same method as the production method of the compound represented by any of general formulae (I) to (III) or a salt thereof.

EXAMPLES

The present invention will be described more specifically with reference to experimental examples and Examples, but the present invention is not limited to these examples. Various modifications are possible by a person skilled in the art within the technical idea of the present invention.

In the examples, the attraction-aggregation activity on cockroaches was determined by a biological test using the above-described linear track olfactometer (FIG. 1).

Example 1

Production of 3,4-dihydro-8-hydroxy-3,7-dimethyl-1H-2-benzopyran-1-one 1-1: Preparation of N-(1,1-dimethylethyl)-2-methoxy-3-methylbenzamide To a solution of 2-methoxy-3-methylbenzoic acid (780 mg, 4.70 mmol) and t-butylamine (600 mg, 8.20 mmol) in dimethylformamide (12 mL) cooled on ice was added 1.5 mL of triethylamine. A BOP reagent (2.26 g, 5.11 mmol) was added. The mixture was stirred at room temperature for 12 hours. Water was poured into the reaction mixture, and extraction with ethyl acetate was performed twice. The organic layer was successively washed with 5% aqueous hydrochloric acid, saturated aqueous sodium bicarbonate, and brine, then dried over magnesium sulfate, and concentrated under reduced pressure. The residue was subjected to silica gel column chromatography to give 900 mg of N-(1,1-dimethylethyl)-2-methoxy-3-methylbenzamide represented by the following formula:

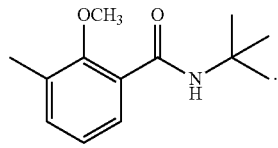 [SMILES: COc1c(C)cccc1C(=O)NC(C)(C)C]

Colorless liquid: $^1$H-NMR (CDCl$_3$, TMS) δ(ppm): 1.47 (s, 9H), 2.32 (s, 3H), 3.77 (s, 3H), 7.11 (dd, 1H), 7.28 (dd, 1H), 7.70 (bs, 1H), 7.86 (dd, 1H).

1-2: Preparation of N-(1,1-dimethylethyl)-2-[2-hydroxypropyl]-5-methyl-6-methoxybenzamide To a solution of N-(1,1-dimethylethyl)-2-methoxy-3-methylbenzamide (1,170 mg, 5.29 mmol) in anhydrous tetrahydrofuran (20 mL) at −78° C. was added 2.0 mL of N,N,N',N'-tetramethylethylenediamine. Then, n-butyllithium (1.6 M solution in n-hexane, 8.7 mL, 13.92 mmol) was added at the same temperature. The mixture was stirred at −78° C. for 1.5 hours. Then, 1.2 mL of propylene oxide was added, and the mixture was stirred at −78° C. for 8 hours. To the reaction mixture, 20 mL of saturated aqueous ammonium chloride solution was added, and extraction with ethyl acetate was performed twice. The organic layer was successively washed with 5% aqueous hydrochloric acid, saturated aqueous sodium bicarbonate, and brine, then dried over magnesium sulfate, and concentrated under reduced pressure. The residue was subjected to silica gel column chromatography to give 290 mg of N-(1,1-dimethylethyl)-2-[2-hydroxypropyl]-5-methyl-6-methoxybenzamide represented by the following formula:

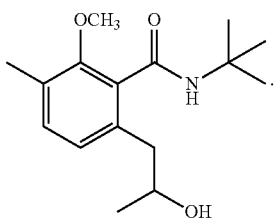 [SMILES: COc1c(C)ccc(CC(C)O)c1C(=O)NC(C)(C)C]

Colorless liquid: $^1$H-NMR (CDCl$_3$, TMS) δ(ppm): 1.27 (d, 3H), 1.47 (s, 9H), 2.26 (s, 3H), 2.62 (dd, 1H), 2.81 (dd, 1H), 3.76 (s, 3H), 3.97 (m, 1H), 4.32 (d, 1H), 6.05 (bs, 1H), 6.92 (d, 1H), 7.14 (d, 1H).

1-3: Preparation of 3,4-dihydro-8-methoxy-3,7-dimethyl-1H-2-benzopyran-1-one To a solution of N-(1,1-dimethylethyl)-2-[2-hydroxypropyl]-5-methyl-6-methoxybenzamide (185 mg, 0.66 mmol) in toluene (5 mL) was added 150 mg of p-toluenesulfonic acid hydrate. The mixture was stirred at 120° C. for 1 hour. To the reaction mixture, 20 mL of ethyl acetate was added. The mixture was washed twice with 5 mL of brine, then dried over magnesium sulfate, and concentrated under reduced pressure. The residue was subjected to silica gel column chromatography to give 290 mg of 3,4-dihydro-8-methoxy-3,7-dimethyl-1H-2-benzopyran-1-one represented by the following formula:

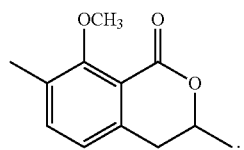

Colorless liquid: $^1$H-NMR (CDCl$_3$, TMS) δ(ppm): 1.48 (d, 3H), 2.30 (s, 3H), 2.80-2.95 (m, 2H), 3.89 (s, 3H), 4.56 (m, 1H), 6.87 (d, 1H), 7.34 (d, 1H).

1-4: Preparation of 3,4-dihydro-8-hydroxy-3,7-dimethyl-1H-2-benzopyran-1-one To a solution of 3,4-dihydro-8-methoxy-3,7-dimethyl-1H-2-benzopyran-1-one (30 mg, 0.15 mmol) in dichloromethane (1.5 mL) at −78° C. was added 0.4 mL of a solution of boron trichloride in dichloromethane (1 M solution). The mixture was stirred at the same temperature for 1.5 hours. To the reaction mixture, 10 mL of ethyl acetate was added. The mixture was washed with 5 mL of brine, then dried over magnesium sulfate, and concentrated under reduced pressure. The residue was subjected to silica gel column chromatography to give 23 mg of 3,4-dihydro-8-hydroxy-3,7-dimethyl-1H-2-benzopyran-1-one represented by the following formula:

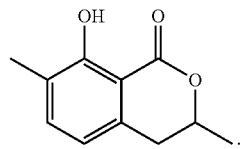

White crystal: $^1$H-NMR (CDCl$_3$, TMS) δ(ppm): 1.52 (d, 3H), 2.25 (s, 3H), 2.90 (d, 2H), 4.71 (m, 1H), 6.60 (d, 1H), 7.27 (d, 1H), 11.26 (s, 1H).

1-5: Preparation of (S)-3, 4-dihydro-8-hydroxy-3,7-dimethyl-1H-2-benzopyran-1-one The reaction was carried out in the same manner as in the above 1-2 except that (S)-propylene oxide was used in place of propylene oxide to give (S)-3,4-dihydro-8-hydroxy-3,7-dimethyl-1H-2-benzopyran-1-one represented by the following formula:

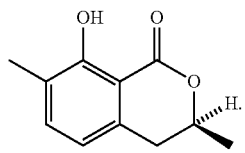

1-6: Preparation of (R)-3,4-dihydro-8-hydroxy-3,7-dimethyl-1H-2-benzopyran-1-one The reaction was carried out in the same manner as in the above 1-2 except that (R)-propylene oxide was used in place of propylene oxide to give (R)-3,4-dihydro-8-hydroxy-3,7-dimethyl-1H-2-benzopyran-1-one represented by the following formula:

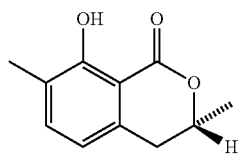

Example 2

Production of 3,4-dihydro-8-hydroxy-7-methyl-1H-2-benzopyran-1-one

The reaction was carried out in the same manner as in the above 1-2 except that ethylene oxide was used in place of propylene oxide to give 3,4-dihydro-8-hydroxy-7-methyl-1H-2-benzopyran-1-one represented by the following formula:

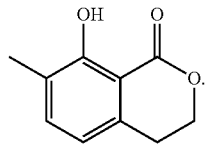

White crystal: $^1$H-NMR (CDCl$_3$, TMS) δ(ppm): 2.25 (s, 3H), 3.02 (dd, 2H), 4.56 (dd, 2H), 6.28 (d, 1H), 7.29 (d, 1H), 11.22 (s, 1H).

Example 3

Production of 3,4-dihydro-8-hydroxy-3-ethyl-7-methyl-1H-2-benzopyran-1-one

The reaction was carried out in the same manner as in Example 1 except that 1,2-epoxybutane was used in place of propylene oxide to give 3,4-dihydro-8-hydroxy-3-ethyl-7-methyl-1H-2-benzopyran-1-one represented by the following formula:

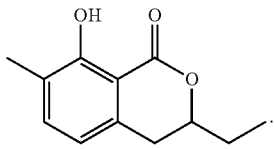

White crystal: $^1$H-NMR (CDCl$_3$, TMS) δ(ppm): 1.10 (t, 3H), 1.75-1.94 (m, 2H), 2.24 (s, 3H), 2.92 (m, 2H), 4.49 (m, 1H), 6.60 (d, 1H), 7.27 (d, 1H), 11.27 (s, 1H).

Example 4

Production of 3,4-dihydro-8-hydroxy-3-ethyl-5,7-dimethyl-1H-2-benzopyran-1-one

The reaction was carried out in the same manner as in Example 1 except that 2-methoxy-3,5-dimethylbenzoic acid was used in place of 2-methoxy-3-methylbenzoic acid and that 1,2-epoxybutane was used in place of propylene oxide to give 3,4-dihydro-8-hydroxy-3-ethyl-5,7-dimethyl-1H-2-benzopyran-1-one represented by the following formula:

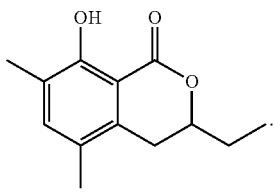 [SMILES: CCC1Cc2c(C)cc(C)c(O)c2C(=O)O1]

White crystal: $^1$H-NMR (CDCl$_3$, TMS) δ(ppm): 1.12 (t, 3H), 1.77-1.95 (m, 2H), 2.17 (s, 3H), 2.22 (s, 3H), 2.70 (dd, 1H), 2.89 (dd, 1H), 4.46 (m, 1H), 7.16 (s, 1H), 11.24 (s, 1H).

Example 5

Production of 3,4-dihydro-8-hydroxy-3-ethyl-6,7-dimethyl-1H-2-benzopyran-1-one

The reaction was carried out in the same manner as in Example 1 except that 2-methoxy-3,4-dimethylbenzoic acid was used in place of 2-methoxy-3-methylbenzoic acid and that 1,2-epoxybutane was used in place of propylene oxide to give 3,4-dihydro-8-hydroxy-3-ethyl-6,7-dimethyl-1H-2-benzopyran-1-one represented by the following formula:

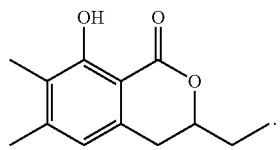 [SMILES: CCC1Cc2cc(C)c(C)c(O)c2C(=O)O1]

White crystal: $^1$H-NMR (CDCl$_3$, TMS) δ(ppm): 1.09 (t, 3H), 1.74-1.93 (m, 2H), 2.16 (s, 3H), 2.28 (s, 3H), 2.80-2.89 (m, 2H), 4.47 (m, 1H), 6.51 (s, 1H), 11.29 (s, 1H).

Example 6

Production of (trans)-3,4-dihydro-8-hydroxy-4,7-dimethyl-3-ethyl-1H-2-benzopyran-1-one and (trans)-3,4-dihydro-8-hydroxy-3,7-dimethyl-4-ethyl-1H-2-benzopyran-1-one 6-1: Preparation of N-(1,1-diethyl)-6-[1-methyl-2-hydroxybutyl]-3-methyl-2-methoxybenzamide and N-(1,1-diethyl)-6-[1-ethyl-2-hydroxypropyl]-3-methyl-2-methoxybenzamide To a solution of N-(1,1-diethyl)-2-methoxy-3-methylbenzamide (1,170 mg, 5.29 mmol) in anhydrous tetrahydrofuran (35 mL) at −78° C. was added s-butyllithium (1.4 M solution in cyclohexane, 4.7 mL, 6.58 mmol). The mixture was stirred at −78° C. for 40 minutes. A solution of 550 mg of cis-2,3-epoxypentane (6.40 mmol) in 5.0 mL of tetrahydrofuran was added, and then 1.3 mL of boron trifluoride dibutyl etherate was added. The mixture was stirred at −78° C. for 4 hours. The mixture was further stirred at room temperature for 12 hours. To the reaction mixture, 20 mL of saturated aqueous ammonium chloride solution was added, and extraction with ethyl acetate was performed twice. The organic layer was washed with brine, then dried over magnesium sulfate, and concentrated under reduced pressure. The residue was subjected to silica gel column chromatography to give 403 mg of a mixture of N-(1,1-diethyl)-6-[1-methyl-2-hydroxybutyl]-3-methyl-2-methoxybenzamide and N-(1,1-diethyl)-6-[1-ethyl-2-hydroxypropyl]-3-methyl-2-methoxybenzamide (about 4:1) represented by the following formulae:

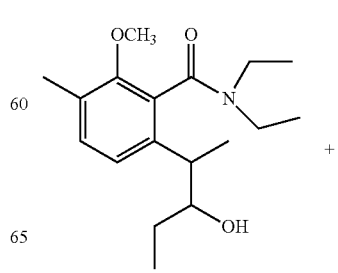

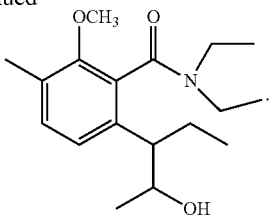

6-2: Preparation of (trans)-3,4-dihydro-8-methoxy-4,7-dimethyl-3-ethyl-1H-2-benzopyran-1-one and (trans)-3,4-dihydro-8-methoxy-3,7-dimethyl-4-ethyl-1H-2-benzopyran-1-one To a solution of 403 mg of the mixture of N-(1,1-diethyl)-6-[1-methyl-2-hydroxybutyl]-3-methyl-2-methoxybenzamide and N-(1,1-diethyl)-6-[1-ethyl-2-hydroxypropyl]-3-methyl-2-methoxybenzamide (about 4:1) in dioxane (8 mL) was added 1.5 mL of concentrated hydrochloric acid. The mixture was stirred at 90° C. for 19 hours. To the reaction mixture, 20 mL of ethyl acetate and 20 mL of ice water were added, and liquid separation was performed. The ethyl acetate layer was washed twice with mL of brine, then dried over magnesium sulfate, and concentrated under reduced pressure. The residue was subjected to silica gel column chromatography to give 99 mg of a mixture of (trans)-3,4-dihydro-8-methoxy-4,7-dimethyl-3-ethyl-1H-2-benzopyran-1-one and (trans)-3,4-dihydro-8-methoxy-3,7-dimethyl-4-ethyl-1H-2-benzopyran-1-one represented by the following formulae:

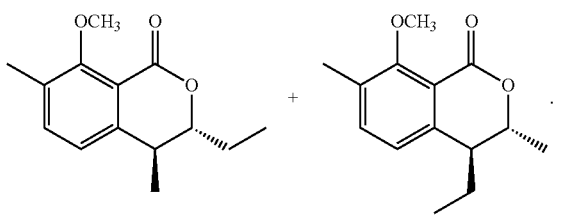

Colorless liquid: $^1$H-NMR (CDCl$_3$, TMS) δ(ppm): 0.96 (t, 3H/5), 1.03 (t, 12H/5), 1.28 (d, 3H/5), 1.34 (d, 12H/5), 1.70 (m, 8H/5), 1.82 (m, 2H/5), 2.30 (s, 12H/5), 2.31 (s, 3H/5), 2.54 (m, 1H/5), 2.91(m, 4H/5), 3.88 (s, 3H/5), 3.89 (s, 12H/5), 4.15 (m, 4H/5), 4.68 (m, 1H/5), 6.88 (d, 1H/5), 6.94 (d, 4H/5), 7.36 (d, 1H).

6-3: Production of (trans)-3,4-dihydro-8-hydroxy-4,7-dimethyl-3-ethyl-1H-2-benzopyran-1-one and (trans)-3,4-dihydro-8-hydroxy-3,7-dimethyl-4-ethyl-1H-2-benzopyran-1-one To a solution of 97 mg of the mixture of (trans)-3,4-dihydro-8-methoxy-4,7-dimethyl-3-ethyl-1H-2-benzopyran-1-one and (trans)-3,4-dihydro-8-methoxy-3,7-dimethyl-4-ethyl-1H-2-benzopyran-1-one in dichloromethane (8 mL) at −78° C. was added 1.5 mL of a solution of boron trichloride in dichloromethane (1 M solution). The mixture was stirred at the same temperature for 0.5 hours. To the reaction mixture, 10 mL of saturated aqueous ammonium chloride solution and 10 mL of ethyl acetate were added, and liquid separation was performed. The ethyl acetate layer was washed with 10 mL of brine, then dried over magnesium sulfate, and concentrated under reduced pressure. The residue was subjected to silica gel column chromatography to give 43.7 mg of (trans)-3,4-dihydro-8-hydroxy-4,7-dimethyl-3-ethyl-1H-2-benzopyran-1-one, as a compound with lower polarity, represented by the following formula:

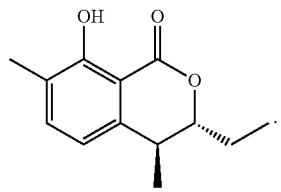 [SMILES: CC[C@H]1OC(=O)c2c(ccc(C)c2O)[C@@H]1C]

White crystal: $^1$H-NMR (CDCl$_3$, TMS) δ(ppm): 1.06 (t, 3H), 1.34 (d, 3H), 1.76 (m, 2H), 2.24 (s, 3H), 2.93 (m, 1H), 4.29 (m, 1H), 6.66 (d, 1H), 7.30 (d, 1H), 11.40 (s, 1H).

Also obtained was 12.7 mg of (trans)-3,4-dihydro-8-hydroxy-3,7-dimethyl-4-ethyl-1H-2-benzopyran-1-one, as a compound with higher polarity, represented by the following formula:

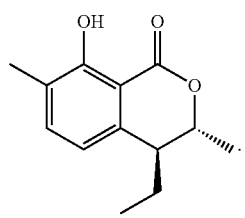

White crystal: $^1$H-NMR (CDCl$_3$, TMS) δ(ppm): 0.94 (t, 3H), 1.37 (d, 3H), 1.66(m, 1H), 1.82 (m, 1H), 2.25 (s, 3H), 2.57 (m, 1H), 4.79 (m, 1H), 6.61 (d, 1H), 7.30 (d, 1H), 11.36 (s, 1H).

Example 7

Production of (trans)-3,4-dihydro-8-hydroxy-3,4,7-trimethyl-1H-2-benzopyran-1-one The reaction was carried out in the same manner as in Example 6 except that cis-2,3-epoxybutane was used in place of cis-2,3-epoxypentane to give (trans)-3,4-dihydro-8-hydroxy-3,4,7-trimethyl-1H-2-benzopyran-1-one represented by the following formula:

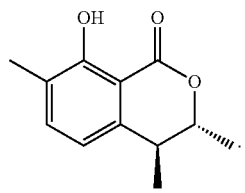

White crystal: $^1$H-NMR (CDCl$_3$, TMS) δ(ppm): 1.34 (d, 3H), 1.47 (d, 3H), 2.25 (s, 3H), 2.85 (m, 1H), 4.47 (m, 1H), 6.67 (d, 1H), 7.32 (d, 1H), 11.40 (s, 1H).

Example 8

Production of (cis)-3,4-dihydro-8-hydroxy-3,4,7-trimethyl-1H-2-benzopyran-1-one The reaction was carried out in the same manner as in Example 6 except that trans-2,3-epoxybutane was used in place of cis-2,3-epoxypentane to give (cis)-3,4-dihydro-8-hydroxy-3,4,7-trimethyl-1H-2-benzopyran-1-one represented by the following formula:

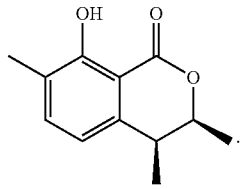

White crystal: $^1$H-NMR (CDCl$_3$, TMS) δ(ppm): 1.20 (d, 3H), 1.43 (d, 3H), 2.25 (s, 3H), 2.90 (m, 1H), 4.76 (m, 1H), 6.62 (d, 1H), 7.30 (d, 1H), 11.27 (s, 1H).

Example 9

Production of (cis)-3,4-dihydro-8-hydroxy-4,7-dimethyl-3-ethyl-1H-2-benzopyran-1-one The reaction was carried out in the same manner as in Example 6 except that trans-2,3-epoxypentane was used in place of cis-2,3-epoxypentane to give (cis)-3,4-dihydro-8-hydroxy-4,7-dimethyl-3-ethyl-1H-2-benzopyran-1-one represented by the following formula:

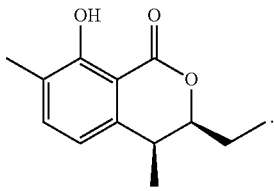 [SMILES: CC[C@@H]1OC(=O)c2c(ccc(C)c2O)[C@@H]1C]

When trans-2,3-epoxypentane was used, the reactivity of the epoxide was low and almost no (cis)-3,4-dihydro-8-hydroxy-3,7-dimethyl-4-ethyl-1H-2-benzopyran-1-one was formed.
White crystal: $^1$H-NMR (CDCl$_3$, TMS) δ(ppm): 1.07 (t, 3H), 1.16 (d, 3H), 1.69 (m, 1H), 1.92 (m, 1H), 2.24 (s, 3H), 2.92 (m, 1H), 4.47 (m, 1H), 6.61 (d, 1H), 7.29 (m, 1H), 11.26 (s, 1H).

Example 10

Production of 3,4-dihydro-8-hydroxy-3-(1-methylpropyl)-5,7-dimethyl-1H-2-benzopyran-1-one 10-1: Preparation of N-(1,1-diethyl)-2-methoxy-3,5-dimethylbenzamide To a solution of 2-methoxy-3,5-dimethylbenzoic acid (2.0 g, 11.11 mmol) and diethylamine (1.3 g, 17.78 mmol) in N,N-dimethylformamide (20 mL) cooled on ice was added 3.2 mL of triethylamine. A BOP reagent (5.9 g, 13.35 mmol) was added. The mixture was stirred at room temperature for 12 hours. Water was poured into the reaction mixture, and extraction with ethyl acetate was performed twice. The organic layer was successively washed with 5% aqueous hydrochloric acid, saturated aqueous sodium bicarbonate, and brine, then dried over magnesium sulfate, and concentrated under reduced pressure. The residue was subjected to silica gel column chromatography to give 1,883 mg of N-(1,1-diethyl)-2-methoxy-3,5-dimethylbenzamide represented by the following formula:

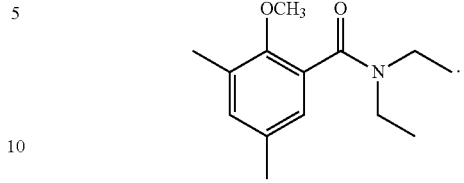

Pale yellow liquid: $^1$H-NMR (CDCl$_3$, TMS) δ(ppm): 1.03 (t, 3H), 1.24 (t, 3H), 2.25 (s, 3H), 2.27 (s, 3H), 3.25 (m, 4H), 3.75 (s, 3H), 6.85 (s, 1H), 6.98 (s, 1H).

10-2: Preparation of N-(1,1-diethyl)-6-[2-hydroxy-3-methylpentyl]-3,5-dimethyl-2-methoxybenzamide To a solution of N-(1,1-diethyl)-2-methoxy-3,5-dimethylbenzamide (1,240 mg, 5.28 mmol) in anhydrous tetrahydrofuran (35 mL) at −78° C. was added s-butyllithium (1.4 M solution in cyclohexane, 4.7 mL, 6.58 mmol). The mixture was stirred at −78° C. for 40 minutes. A solution of 650 mg of 1,2-epoxy-3-methylpentane (6.50 mmol) in 5.0 mL of tetrahydrofuran was added, and then 1.3 mL of boron trifluoride dibutyl etherate was added. The mixture was stirred at −78° C. for 4 hours. The mixture was further stirred at room temperature for 12 hours. To the reaction mixture, 20 mL of saturated aqueous ammonium chloride solution was added, and extraction with ethyl acetate was performed twice. The organic layer was washed with brine, then dried over magnesium sulfate, and concentrated under reduced pressure. The residue was subjected to silica gel column chromatography to give 548 mg of N-(1,1-diethyl)-6-[2-hydroxy-3-methylpentyl]-3,5-dimethyl-2-methoxybenzamide represented by the following formula:

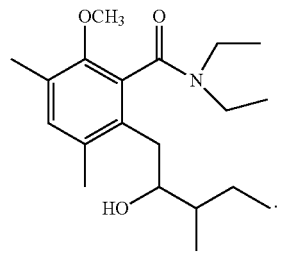 [SMILES: CCC(C)C(O)Cc1c(C)cc(C)c(OC)c1C(=O)N(CC)CC]

10-3: Preparation of 3,4-dihydro-8-methoxy-3-[1-methylpropyl]-5,7-dimethyl-1H-2-benzopyran-1-one To a solution of 424 mg of N-(1,1-diethyl)-6-[2-hydroxy-3-methylpentyl]-3,5-dimethyl-2-methoxybenzamide in dioxane (15 mL) was added 2.0 mL of concentrated hydrochloric acid. The mixture was stirred at 90° C. for 26 hours. To the reaction mixture, 20 mL of ethyl acetate and 20 mL of ice water were added, and liquid separation was performed. The ethyl acetate layer was washed twice with mL of brine, then dried over magnesium sulfate, and concentrated under reduced pressure. The residue was subjected to silica gel column chromatography to give 118 mg of 3,4-dihydro-8-methoxy-3-[1-methylpropyl]-5,7-dimethyl-1H-2-benzopyran-1-one (racemic mixture of diastereomers) represented by the following formula:

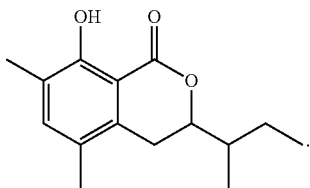 [SMILES: CCC(C)C1Cc2c(C)cc(C)c(O)c2C(=O)O1]

Colorless liquid: $^1$H-NMR (CDCl$_3$, TMS) δ(ppm): 0.95 (t, 3H), 1.03 (d, 1.2H), 1.08 (d, 1.8H), 1.3-1.9 (m, 3H), 2.23 (s, 3H), 2.27 (s, 3H), 2.75 (m, 2H), 3.86 (s, 3H), 4.20 (m, 1H), 7.20 (s, 1H).

10-4: Production of 3,4-dihydro-8-hydroxy-3-[1-methylpropyl]-5,7-dimethyl-1H-2-benzopyran-1-one To a solution of 113 mg of 3,4-dihydro-8-methoxy-3-[1-methylpropyl]-5,7-dimethyl-1H-2-benzopyran-1-one in dichloromethane (8 mL) at −78° C. was added a solution of boron trichloride in 1.5 mL of dichloromethane (1 M solution). The mixture was stirred at the same temperature for 0.5 hours. To the reaction mixture, 10 mL of saturated aqueous ammonium chloride solution and 10 mL of ethyl acetate were added, and liquid separation was performed. The ethyl acetate layer was washed with 10 mL of brine, then dried over magnesium sulfate, and concentrated under reduced pressure. The residue was subjected to silica gel column chromatography to give 45.6 mg of 3,4-dihydro-8-hydroxy-3-[1-methylpropyl]-5,7-dimethyl-1H-2-benzopyran-1-one (racemic mixture of diastereomers) represented by the following formula:

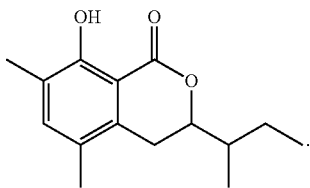 [SMILES: CCC(C)C1Cc2c(C)cc(C)c(O)c2C(=O)O1]

Colorless liquid: $^1$H-NMR (CDCl$_3$, TMS) δ(ppm): 0.97 (t, 3H), 1.04 (d, 1.2H), 1.08 (d, 1.8H), 1.34 (m, 1H), 1.69 (m, 1H), 1.80 (m, 0.6H), 1.90 (m, 0.4H), 2.17 (s, 3H), 2.22 (s, 3H), 2.80 (m, 2H), 4.38 (m, 0.4H), 4.41 (m, 0.6H), 7.16 (s, 1H), 11.23 (s, 1H).

Example 11

Production of 3,4-dihydro-8-hydroxy-3-[1-methylbutyl]-5,7-dimethyl-1H-2-benzopyran-1-one The reaction was carried out in the same manner as in Example 10 except that 1,2-epoxy-3-methylhexane was used in place of 1,2-epoxy-3-methylpentane to give 3,4-dihydro-8-hydroxy-3-[1-methylbutyl]-5,7-dimethyl-1H-2-benzopyran-1-one (racemic mixture of diastereomers) represented by the following formula:

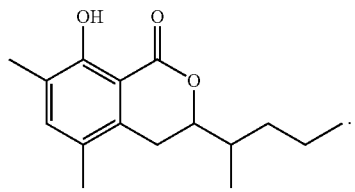 [SMILES: CCCC(C)C1Cc2c(C)cc(C)c(O)c2C(=O)O1]

Colorless liquid: $^1$H-NMR (CDCl$_3$, TMS) δ(ppm): 0.94 (m, 3H), 1.04 (d, 3H/3), 1.07 (d, 6H/3), 1.30 (m, 2H), 1.46 (m, 1H), 1.60 (m, 1H), 1.87 (m, 2H/3), 1.98 (m, 1H/3), 2.17 (s, 3H), 2.22 (s, 3H), 2.78 (m, 2H), 4.40 (m, 1H), 7.16 (s, 1H), 11.23 (s, 1H).

Example 12

Production of 3,4-dihydro-8-hydroxy-3-methyl-7-methoxy-1H-2-benzopyran-1-one

The reaction was carried out in the same manner as in Example 10 except that 2,3-dimethoxybenzoic acid was used in place of 2-methoxy-3,5-dimethylbenzoic acid and that propylene oxide was used in place of 1,2-epoxy-3-methylpentane to give 3,4-dihydro-8-hydroxy-3-methyl-7-methoxy-1H-2-benzopyran-1-one represented by the following formula:

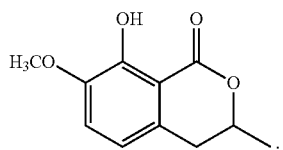

White crystal: $^1$H-NMR (CDCl$_3$, TMS) δ(ppm): 1.54 (d, 3H), 2.89 (d, 2H), 3.90 (s, 3H), 4.73 (m, 1H), 6.64 (d, 1H), 7.01 (d, 1H), 11.25 (s, 1H).

Example 13

Production of 3,4-dihydro-8-hydroxy-3-methyl-7-ethyl-1H-2-benzopyran-1-one 13-1: Preparation of N-(1,1-diethyl)-2-methoxy-3-ethylbenzamide The reaction was carried out in the same manner as in Example 10 except that 2-methoxy-3-ethylbenzoic acid was used in place of 2-methoxy-3,5-dimethylbenzoic acid to give N-(1,1-diethyl)-2-methoxy-3-ethylbenzamide represented by the following formula:

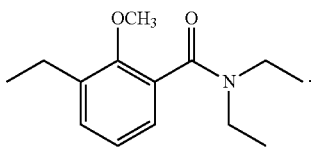 [SMILES: CCc1cccc(C(=O)N(CC)CC)c1OC]

Colorless liquid: $^1$H-NMR (CDCl$_3$, TMS) δ(ppm): 1.03 (t, 3H), 1.23 (t, 3H), 1.27 (t, 3H), 2.68 (q, 2H), 3.15 (q, 2H), 3.48 (q, 2H), 3.80 (s, 3H), 7.06 (d, 1H), 7.07 (d, 1H), 7.21 (dd, 1H).

13-2: Production of 3,4-dihydro-8-hydroxy-3-methyl-7-ethyl-1H-2-benzopyran-1-one The reaction was carried out in the same manner as in Example 10 except that N-(1,1-diethyl)-2-methoxy-3-ethyl-benzamide was used in place of N-(1,1-diethyl)-2-methoxy-3,5-dimethylbenzamide and that propylene oxide was used in place of 1,2-epoxy-3-methylpentane to give 3,4-dihydro-8-hydroxy-3-methyl-7-ethyl-1H-2-benzopyran-1-one represented by the following formula:

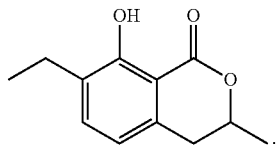

White crystal: $^{1}$H-NMR (CDCl$_3$, TMS) δ(ppm): 1.22 (t, 3H), 1.53 (d, 3H), 2.67 (q, 2H), 2.90 (d, 2H), 4.71 (m, 1H), 6.63 (d, 1H), 7.29 (d, 1H), 11.29 (s, 1H).

Example 14

Production of (trans)-5-bromo-3,4-dihydro-8-hydroxy-3,4,7-trimethyl-1H-2-benzopyran-1-one

14-1: Preparation of (trans)-5-bromo-3,4-dihydro-8-methoxy-3,4, 7-trimethyl-1H-2-benzopyran-1-one To a solution of (trans)-3,4-dihydro-8-methoxy-3,4,7-trimethyl-1H-2-benzopyran-1-one (10 mg, 0.05 mmol) (represented by the following formula:

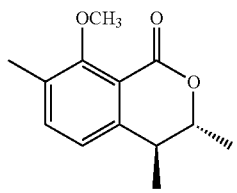

[colorless liquid: $^{1}$H-NMR (CDCl$_3$, TMS) δ(ppm): 1.34 (d, 3H), 1.42 (d, 3H), 2.31 (s, 3H), 2.82 (m, 1H), 3.89 (s, 3H), 4.32 (m, 1H), 6.96 (d, 1H), 7.38 (d, 1H)]) in acetonitrile (0.5 mL) at room temperature was added N-bromosuccinimide (16 mg, 0.09 mmol). The mixture was stirred at the same temperature for 17 hours. To the reaction mixture, 10 mL of ethyl acetate and 10 mL of water were added, and liquid separation was performed. The ethyl acetate layer was washed with 5 mL of brine, then dried over magnesium sulfate, and concentrated under reduced pressure to give 15 mg of (trans)-5-bromo-3,4-dihydro-8-methoxy-3,4,7-trimethyl-1H-2-benzopyran-1-one, as a crude product, represented by the following formula:

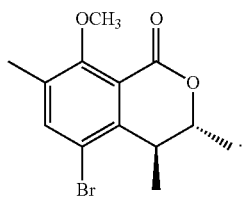

14-2: Production of (trans)-5-bromo-3,4-dihydro-8-hydroxy-3,4, 7-trimethyl-1H-2-benzopyran-1-one The crude product ((trans)-5-bromo-3,4-dihydro-8-methoxy-3,4,7-trimethyl-1H-2-benzopyran-1-one) (15 mg, 0.05 mmol) was subjected to the same operation as in the above 10-4 to give 12 mg of (trans)-5-bromo-3,4-dihydro-8-hydroxy-3,4,7-trimethyl-1H-2-benzopyran-1-one represented by the following formula:

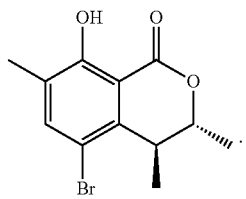

Colorless liquid: $^{1}$H-NMR (CDCl$_3$, TMS) δ(ppm): 1.34 (d, 3H), 1.35 (d, 3H), 2.24 (s, 3H), 3.14 (m, 1H), 4.74 (m, 1H), 7.52 (s, 1H), 11.53 (s, 1H).

Example 15

Production of (trans)-5-chloro-3,4-dihydro-8-hydroxy-3,4,7-trimethyl-1H-2-benzopyran-1-one The reaction was carried out in the same manner as in Example 14 except that N-chlorosuccinimide was used in place of N-bromosuccinimide in the above 14-1, that ethyl acetate was used in place of acetonitrile as the solvent, and that the reaction temperature was changed from room temperature to 80° C. to give (trans)-5-chloro-3,4-dihydro-8-hydroxy-3,4,7-trimethyl-1H-2-benzopyran-1-one represented by the following formula:

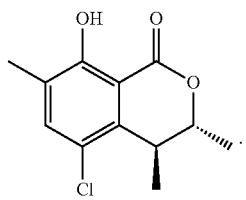

White crystal: $^{1}$H-NMR (CDCl$_3$, TMS) δ(ppm): 1.35 (d, 3H), 1.55 (d, 3H), 2.25 (s, 3H), 3.18 (m, 1H), 4.75 (m, 1H), 7.36 (s, 1H), 11.47 (s, 1H).

Example 16

Production of 3,4-dihydro-8-hydroxy-3-[1-methyl-2-propenyl]-5,7-dimethyl-1H-2-benzopyran-1-one The reaction was carried out in the same manner as in Example 10 except that 1,2-epoxy-3-methyl-4-pentene was used in place of 1,2-epoxy-3-methylpentane to give 3,4-dihydro-8-hydroxy-3-[1-methyl-2-propenyl]-5,7-dimethyl-1H-2-benzopyran-1-one represented by the following formula:

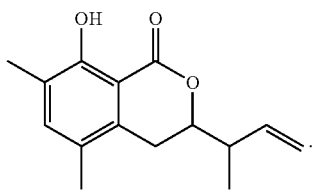 [SMILES: C=CC(C)C1Cc2c(C)cc(C)c(O)c2C(=O)O1]

White crystal: $^1$H-NMR (CDCl$_3$, TMS) δ(ppm): 1.23 (d, 3H), 2.15 (s, 3H), 2.22 (s, 3H), 2.75 (m, 3H), 4.39 (m, 1H), 5.17 (m, 2H), 5.86 (m, 1H), 7.15 (s, 1H), 11.19 (s, 1H).

Example 17

Production of 2,3,3a,9b-tetrahydro-6-hydroxy-7-methyl-cyclopenta[c][2]benzopyran-5(1H)-one The reaction was carried out in the same manner as in Example 10 except that N-(1,1-diethyl)-2-methoxy-3-methylbenzamide was used in place of N-(1,1-diethyl)-2-methoxy-3,5-dimethylbenzamide and that cyclopentane oxide (mixture of cis- and trans-isomers) was used in place of 1,2-epoxy-3-methylpentane to give 2,3,3a,9b-tetrahydro-6-hydroxy-7-methyl-cyclopenta[c][2]benzopyran-5(1H)-one represented by the following formula:

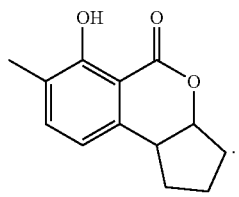 [SMILES: Cc1ccc2c(c1O)C(=O)OC1CCCC21]

White crystal: $^1$H-NMR (CDCl$_3$, TMS) δ(ppm): 1.32 (m, 2H), 1.95 (m, 2H), 2.20 (m, 2H), 2.26 (s, 3H), 2.97 (dt, 1H), 4.24 (m, 1H), 6.55 (d, 1H), 7.29 (d, 1H), 11.23 (s, 1H).

Example 18

Production of 7-hydroxy-6-methyl-1(3H)-isobenzofuranone 18-1: Preparation of N-(1,1-diethyl)-6-formyl-3-methyl-2-methoxybenzamide To a solution of N-(1,1-diethyl)-2-methoxy-3-methylbenzamide (1,050 mg, 4.76 mmol) in anhydrous tetrahydrofuran (16 mL) at −78° C. were successively added N,N,N',N'-tetramethylethylenediamine (0.85 mL, 5.72 mmol) and s-butyllithium (1.4 M solution in cyclohexane, 4.09 mL, 5.72 mmol). The mixture was stirred at −78° C. for 1 hour. N,N-dimethylformamide (0.46 mL, 5.95 mmol) was added. The mixture was stirred at −78° C. for 4 hours. The mixture was further stirred at room temperature for 12 hours. To the reaction mixture cooled on ice, 20 mL of 5% aqueous hydrochloric acid was added, and extraction with ethyl acetate was performed twice. The organic layer was successively washed with saturated aqueous sodium bicarbonate and brine, then dried over magnesium sulfate, and concentrated under reduced pressure to give 556 mg of N-(1,1-diethyl)-6-formyl-3-methyl-2-methoxybenzamide, as a crude product, represented by the following formula:

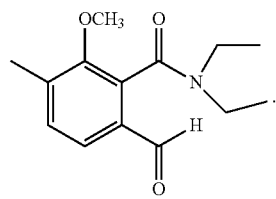 [SMILES: CCN(CC)C(=O)c1c(C=O)ccc(C)c1OC]

18-2: Preparation of 7-methoxy-6-methyl-1(3H)-isobenzofuranone

To a solution of the crude product (N-(1,1-diethyl)-6-formyl-3-methyl-2-methoxybenzamide) (556 mg) in methanol (15 mL) cooled on ice was added sodium borohydride (130 mg, 3.44 mmol). The mixture was allowed to warm to room temperature and stirred for 1 hour. To the mixture cooled on ice, 4 mL of 5% aqueous hydrochloric acid was added. The mixture was stirred at 100° C. for 9 hours. The reaction mixture was allowed to cool back to room temperature. To the reaction mixture, ice water was added, and extraction with ethyl acetate was performed twice. The organic layer was washed with brine, then dried over magnesium sulfate, and concentrated under reduced pressure to give 429 mg of 7-methoxy-6-methyl-1(3H)-isobenzofuranone, as a crude product, represented by the following formula:

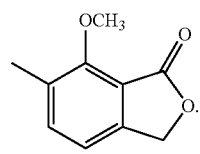

18-3: Preparation of 7-hydroxy-6-methyl-1(3H)-isobenzofuranone

To a solution of the crude product (7-methoxy-6-methyl-1(3H)-isobenzofuranone) (55 mg) in dichloromethane (2.0 mL) at −78° C. was added 0.7 mL of a solution of boron tribromide in dichloromethane (1 M solution). The mixture was stirred at the same temperature for 1 hour. The mixture was further stirred at room temperature for 12 hours. To the reaction mixture, cold water was added, and extraction with ethyl acetate was performed twice. The organic layer was washed with brine, then dried over magnesium sulfate, and concentrated under reduced pressure. The residue was subjected to silica gel column chromatography to give 20 mg of 7-hydroxy-6-methyl-1(3H)-isobenzofuranone represented by the following formula:

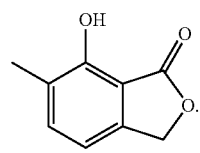

White solid: $^1$H-NMR (CDCl$_3$, TMS) δ(ppm): 2.23 (s, 3H), 5.28 (s, 2H), 6.86 (d, 1H), 7.41 (d, 1H), 7.87 (s, 1H).

Example 19

Production of 7-hydroxy-3,6-dimethyl-1(3H)-isobenzofuranone

19-1: Preparation of N-(1,1-diethyl)-6-(1-hydroxyethyl)-3-methyl-2-methoxybenzamide To a solution of the crude product (N-(1,1-diethyl)-6-formyl-3-methyl-2-methoxybenzamide) (124 mg) in anhydrous tetrahydrofuran (2.7 mL) cooled on ice was added methyl magnesium bromide (0.9 M solution in tetrahydrofuran, 0.75 mL, 0.68 mmol). The mixture was allowed to warm to room temperature and stirred for 14 hours. To the reaction mixture cooled on ice, 4 mL of 5% aqueous hydrochloric acid and 10 mL of water were added, and extraction with ethyl acetate was performed twice. The organic layer was successively washed with saturated aqueous sodium bicarbonate and brine, then dried over magnesium sulfate, and concentrated under reduced pressure to give 70 mg of N-(1,1-diethyl)-6-(1-hydroxy-ethyl)-3-methyl-2-methoxybenzamide, as a crude product, represented by the following formula:

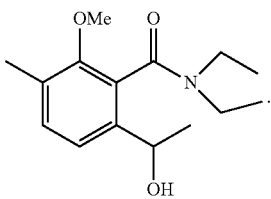 [SMILES: CCN(CC)C(=O)c1c(C(C)O)ccc(C)c1OC]

19-2: Preparation of 7-methoxy-3,6-dimethyl-1(3H)-isobenzofuranone

To a solution of 70 mg of the crude product (N-(1,1-diethyl)-6-(1-hydroxy-ethyl)-3-methyl-2-methoxybenzamide) in dioxane (5 mL) was added 1.0 mL of concentrated hydrochloric acid. The mixture was stirred at 90° C. for 8 hours. To the reaction mixture, 20 mL of ethyl acetate and 10 mL of ice water were added, and liquid separation was performed. The ethyl acetate layer was washed twice with 10 mL of brine, then dried over magnesium sulfate, and concentrated under reduced pressure. The residue was subjected to silica gel column chromatography to give 42 mg of 7-methoxy-3,6-dimethyl-1(3H)-isobenzofuranone, as a crude product, represented by the following formula:

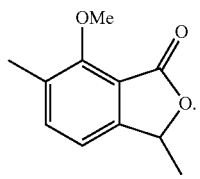

19-3: Preparation of 7-hydroxy-3,6-dimethyl-1(3H)-isobenzofuranone

To a solution of the crude product (7-methoxy-3,6-dimethyl-1(3H)-isobenzofuranone) (42 mg) in dichloromethane (2.0 mL) at −78° C. was added 0.5 mL of a solution of boron tribromide in dichloromethane (1 M solution). The mixture was stirred at the same temperature for 30 minutes. The mixture was further stirred at room temperature for 13 hours. To the reaction mixture, cold water was added, and extraction with ethyl acetate was performed twice. The organic layer was washed with brine, then dried over magnesium sulfate, and concentrated under reduced pressure. The residue was subjected to silica gel column chromatography to give 30 mg of 7-hydroxy-3,6-dimethyl-1(3H)-isobenzofuranone represented by the following formula:

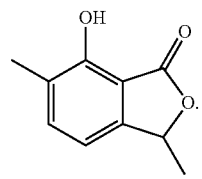

Colorless liquid: $^1$H-NMR (CDCl$_3$, TMS) δ(ppm): 1.62 (d, 3H), 2.29 (s, 3H), 5.54 (q, 1H), 6.80 (d, 1H), 7.41 (d, 1H), 7.90 (s, 1H).

Example 20

Production of 3,4-dihydro-4,5,7-trimethyl-8-hydroxy-1(2H)-naphthalenone

To a solution of 2,4-dimethylanisole (2.0 g, 14.7 mmol) and 4-hydroxypentanoic acid lactone (1.8 g, 18.0 mmol) in dichloromethane (7.0 mL) cooled on ice was added dropwise titanium tetrachloride (1.0 M solution in dichloromethane, 25.0 mL, 25.0 mmol). The mixture was stirred at 40° C. for 25 hours. Cold water was poured into the reaction mixture, and extraction with ethyl acetate was performed twice. The organic layer was washed with brine, then dried over magnesium sulfate, and concentrated under reduced pressure. The residue was subjected to silica gel column chromatography to give 116 mg of 3,4-dihydro-4,5,7-trimethyl-8-hydroxy-1(2H)-naphthalenone represented by the following formula:

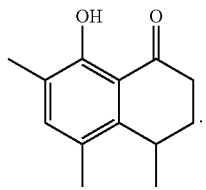

Yellow liquid: $^1$H-NMR (CDCl$_3$, TMS) δ(ppm): 1.26 (d, 3H), 1.97 (m, 1H), 2.19 (s, 3H), 2.21 (m, 1H), 2.24 (s, 3H), 2.59 (m, 1H), 2.91 (m, 1H), 3.24 (m, 1H), 7.15 (s, 1H), 12.94 (s, 1H).

Example 21

Production of 3,4-dihydro-3,5,7-trimethyl-8-hydroxy-1(2H)-naphthalenone

21-1: Preparation of 3,5-dimethyl-2-methoxybenzaldehyde and 2,4-dimethyl-5-methoxybenzaldehyde To a solution of 2,4-dimethylanisole (3.0 g, 22.1 mmol) and dichloromethyl methyl ether (2.4 g, 20.9 mmol) in dichloromethane (5.0 mL) cooled on ice was added dropwise titanium tetrachloride (1.0 M solution in dichloromethane, 30.0 mL, 30.0 mmol). The mixture was stirred under cooling on ice for 1 hour. The reaction mixture was poured into cold water, and extraction with ethyl acetate was performed twice. The organic layer was washed with brine, then dried over magnesium sulfate, and concentrated under reduced pressure to give 3.1 g of a mixture of 3,5-dimethyl-2-methoxybenzaldehyde and 2,4-dimethyl-5-methoxybenzaldehyde (about 4:1), as a crude product, represented by the following formulae:

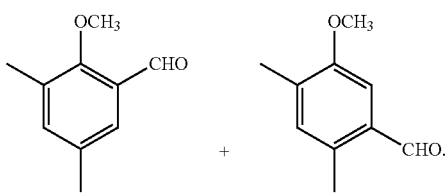

21-2: Preparation of 1-(3,5-dimethyl-2-methoxyphenyl)-2-propanone and 1-(2,4-dimethyl-5-methoxyphenyl)-2-propanone To a solution of the crude product (the mixture of 3,5-dimethyl-2-methoxybenzaldehyde and 2,4-dimethyl-5-methoxybenzaldehyde (about 4:1)) (3.1 g) and ammonium acetate (3.5 g, 45.4 mmol) in acetic acid (13.0 mL) cooled on ice was added dropwise nitroethane (9.6 mL, 134.3 mmol). The mixture was stirred at 100° C. for 2.5 hours. Cold water and saturated aqueous sodium bicarbonate were poured into the reaction mixture to neutralize it. Extraction with ethyl acetate was performed twice. The organic layer was washed with brine, then dried over magnesium sulfate, and concentrated under reduced pressure to give 3.89 g of a crude product. To a solution of the crude product (3.89 g) in water (20.0 mL) and methanol (60.0 mL) cooled on ice were added dropwise iron powder (10 to 20 mesh, 4.4 g, 78.7 mmol) and then concentrated hydrochloric acid (36% aqueous solution, 21.6 mL). The mixture was stirred at 70° C. for 4 hours. Cold water and 10% aqueous sodium hydroxide solution were poured into the reaction mixture to neutralize it. Extraction with ethyl acetate was performed twice. The organic layer was washed with brine, then dried over magnesium sulfate, and concentrated under reduced pressure. The residue was subjected to silica gel column chromatography to give 1.1 g of a mixture of 1-(3,5-dimethyl-2-methoxyphenyl)-2-propanone and 1-(2,4-dimethyl-5-methoxyphenyl)-2-propanone represented by the following formulae:

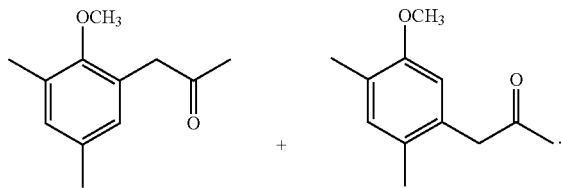

21-3: Preparation of ethyl 3-methyl-4-(3,5-dimethyl-2-methoxyphenyl)-2-butenoate and ethyl 3-methyl-4-(2,4-dimethyl-5-methoxyphenyl)-2-butenoate To a solution of the mixture of 1-(3,5-dimethyl-2-methoxyphenyl)-2-propanone and 1-(2,4-dimethyl-5-methoxyphenyl)-2-propanone (1.1 g, 5.7 mmol) and ethyl diethylphosphonoacetate (1.4 g, 6.2 mmol) in toluene (6.0 mL) cooled on ice was added dropwise a solution of 20% sodium ethoxide in ethanol (1.7 g, 6.3 mmol). The mixture was stirred at 60° C. for 6 hours. Cold water was poured into the reaction mixture, and extraction with ethyl acetate was performed twice. The organic layer was washed with brine, then dried over magnesium sulfate, and concentrated under reduced pressure. The residue was subjected to silica gel column chromatography to give 1.1 g of a mixture of ethyl 3-methyl-4-(3,5-dimethyl-2-methoxyphenyl)-2-butenoate and ethyl 3-methyl-4-(2,4-dimethyl-5-methoxyphenyl)-2-butenoate represented by the following formulae:

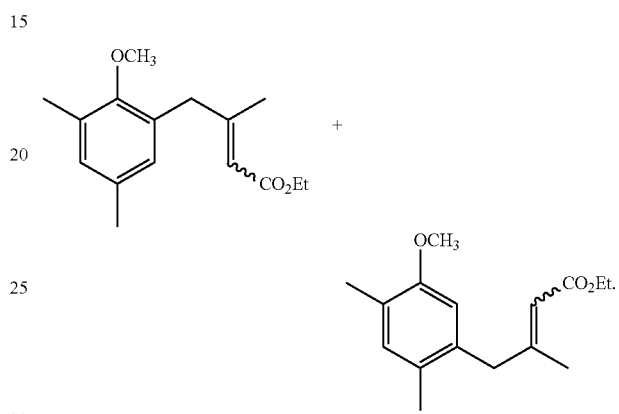

21-4: Preparation of ethyl 3-methyl-4-(3,5-dimethyl-2-methoxyphenyl)-butanoate and ethyl 3-methyl-4-(2,4-dimethyl-5-methoxyphenyl)-butanoate To a solution of the mixture of ethyl 3-methyl-4-(3,5-dimethyl-2-methoxyphenyl)-2-butenoate and ethyl 3-methyl-4-(2,4-dimethyl-5-methoxyphenyl)-2-butenoate (955 mg, 3.6 mmol) in ethyl acetate (8.0 mL) at room temperature was added palladium on carbon (160 mg). The system was replaced with hydrogen gas. The reaction mixture was stirred at room temperature for 8 hours. The reaction mixture was filtrated through Celite with ethyl acetate. The filtrate was concentrated under reduced pressure to give 926 mg of a mixture of ethyl 3-methyl-4-(3,5-dimethyl-2-methoxyphenyl)-butanoate and ethyl 3-methyl-4-(2,4-dimethyl-5-methoxyphenyl)-butanoate, as a crude product, represented by the following formulae:

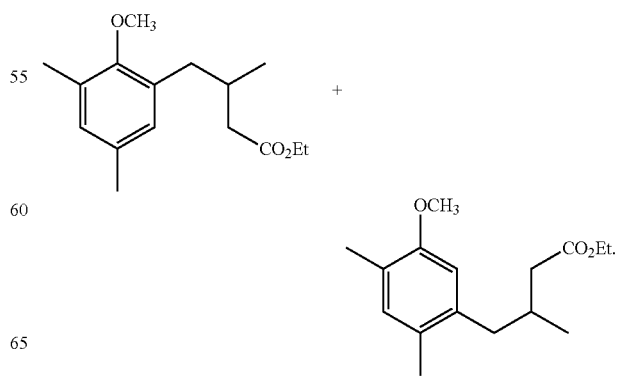

21-5: Preparation of 3,4-dihydro-3,6,8-trimethyl-5-methoxy-1(2H)-naphthalenone and 3,4-dihydro-3,5,7-trimethyl-8-methoxy-1(2H)-naphthalenone To a solution of the crude product (the mixture of ethyl 3-methyl-4-(3,5-dimethyl-2-methoxyphenyl)-butanoate and ethyl 3-methyl-4-(2,4-dimethyl-5-methoxyphenyl)-butanoate) (926 mg) in chloroform (15.0 mL) cooled on ice was added dropwise trifluoromethanesulfonic acid (25.0 g, 165.0 mmol). The mixture was stirred at room temperature for 24 hours. The reaction mixture was poured into ice water, and extraction with diethyl ether was performed twice. The organic layer was washed with brine, then dried over magnesium sulfate, and concentrated under reduced pressure. The residue was subjected to silica gel column chromatography to give 140 mg of a mixture of 3,4-dihydro-3,6,8-trimethyl-5-methoxy-1(2H)-naphthalenone and 3,4-dihydro-3,5,7-trimethyl-8-methoxy-1(2H)-naphthalenone represented by the following formulae:

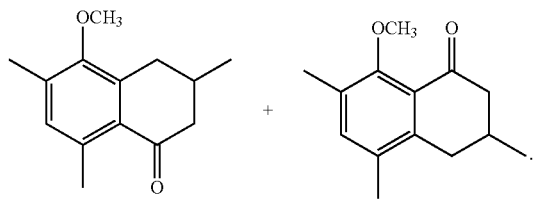

21-6: Production of 3,4-dihydro-3,5,7-trimethyl-8-hydroxy-1(2H)-naphthalenone To a solution of the mixture of 3,4-dihydro-3,6,8-trimethyl-5-methoxy-1(2H)-naphthalenone and 3,4-dihydro-3,5,7-trimethyl-8-methoxy-1(2H)-naphthalenone (140 mg) in dichloromethane (10.0 mL) at −78° C. was added 2.0 mL of a solution of boron trichloride in dichloromethane (1 M solution). The mixture was stirred at the same temperature for 30 minutes. The reaction mixture was allowed to warm to room temperature. Cold water and saturated aqueous ammonium chloride solution were poured into the reaction mixture, and extraction with ethyl acetate was performed twice. The organic layer was washed with brine, then dried over magnesium sulfate, and concentrated under reduced pressure. The residue was subjected to silica gel column chromatography to give 106 mg of 3,4-dihydro-3,5,7-trimethyl-8-hydroxy-1(2H)-naphthalenone represented by the following formula:

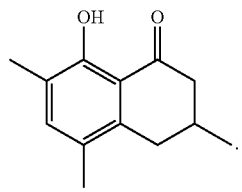

White solid: $^1$H-NMR (CDCl$_3$, TMS) δ(ppm): 1.16 (d, 3H), 2.18 (s, 3H), 2.20 (s, 3H), 2.32 (m, 3H), 2.70 (d, 1H), 2.92 (d, 1H), 7.15 (s, 1H), 12.68 (s, 1H).

Example 22

Production of 3,4-dihydro-3,4,5,7-tetramethyl-8-hydroxy-1(2H)-naphthalenone and 2,3-dihydro-3-ethyl-7-hydroxy-3,4,6-trimethyl-1H-inden-1-one The reaction was carried out in the same manner as in Example 20 except that 4-hydroxy-3-methylpentanoic acid lactone was used in place of 4-hydroxypentanoic acid lactone, followed by silica gel chromatography, to give 150 mg of 3,4-dihydro-3,4,5,7-tetramethyl-8-hydroxy-1(2H)-naphthalenone, as a compound with lower polarity, represented by the following formula:

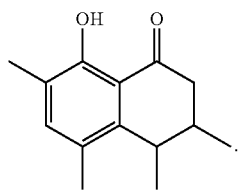

Yellow liquid: $^1$H-NMR (CDCl$_3$, TMS) δ(ppm): 1.01 (d, 3H), 1.28 (d, 3H), 2.19 (s, 3H), 2.23 (s, 3H), 2.25 (m, 2H), 2.98 (m, 1H), 3.06 (dd, 1H), 7.16 (s, 1H), 12.91 (s, 1H).

Also obtained was 104 mg of 2,3-dihydro-3-ethyl-7-hydroxy-3,4,6-trimethyl-1H-inden-1-one, as a compound with higher polarity, represented by the following formula:

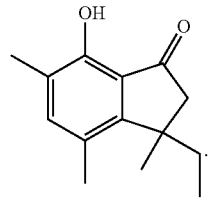 [SMILES: CCC1(C)CC(=O)c2c(O)c(C)cc(C)c21]

Yellow liquid: $^1$H-NMR (CDCl$_3$, TMS) δ(ppm): 0.71 (t, 3H), 1.46 (s, 3H), 1.79 (m, 1H), 1.89 (m, 1H), 2.20 (s, 3H), 2.32 (s, 3H), 2.45 (d, 1H), 2.70 (d, 1H), 7.10 (s, 1H), 9.51 (s, 1H).

Test Example 1

Biological Test

Each of the compounds produced in Example 5 described above, and Example 23 and Comparative Example 1 described below was assessed by a biological test using the linear track olfactometer at doses ranging from 10$^{-3}$ pg to 10$^6$ pg to determine the attraction-aggregation activity on cockroaches.

Example 23

A compound represented by the formula:

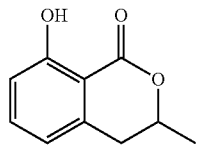

(compound name: mellein, produced by Funakoshi) was assessed by the test.

Comparative Example 1

The compound obtained before hydrolysis in the production in Example 5, being represented by the formula:

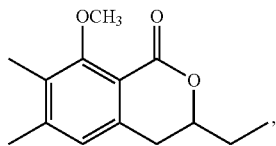

was assessed by the test.

Figure 2:
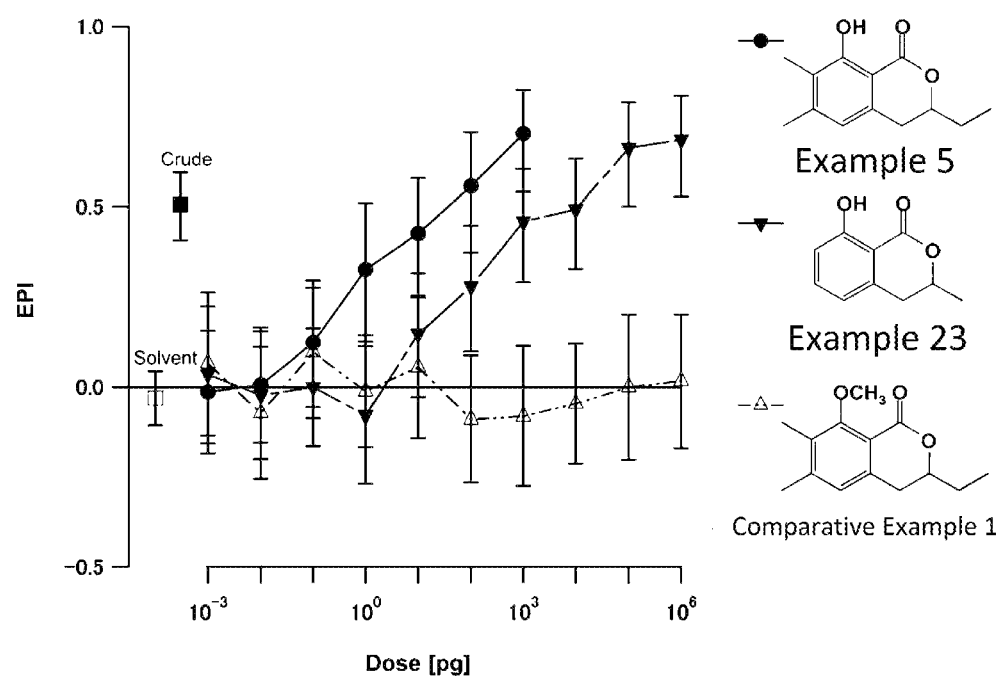
FIG. 2 is a chart showing the results of the biological test for determining attraction-aggregation activity on cockroaches using the linear track olfactometer in Test Example 1. In the chart, the term "EPI" represents the degree of the attraction-aggregation activity on cockroaches, and the term "Dose" represents the doses of the compounds used in the test.

FIG. 2 shows the results of the biological test in Test Example 1 (Example 5, Example 23, and Comparative Example 1).

The compounds of Example 5 and Example 23 as practical embodiments of the present invention showed high attraction-aggregation activity on cockroaches. In contrast, the compound of Comparative Example 1 showed no activity even at a dose of 10,000 times ($10^6$ pg) the dose ($10^2$ pg) at which the compound of Example 5 had an EPI value of about 0.5.

Test Example 2

Biological Test

Each of the compounds produced in step 1-4 of Example 1, and Example 3 was assessed by a biological test using the linear track olfactometer at doses ranging from $10^{-3}$ pg to $10^3$ pg to determine the attraction-aggregation activity on cockroaches.

Figure 3:
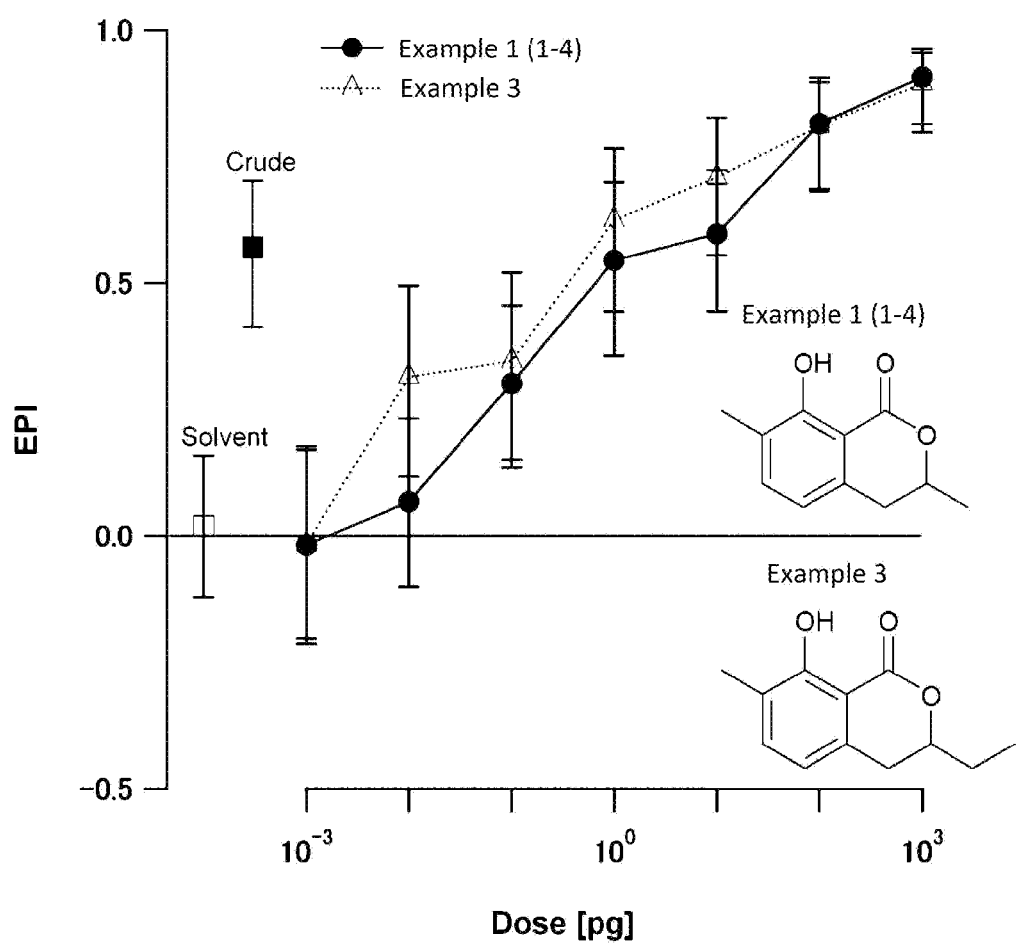
FIG. 3 is a chart showing the results of the biological test for determining attraction-aggregation activity on cockroaches using the linear track olfactometer in Test Example 2.

FIG. 3 shows the results of the biological test in Test Example 2 (step 1-4 of Example 1, and Example 3).

The compounds of step 1-4 of Example 1, and Example 3 as practical embodiments of the present invention showed high attraction-aggregation activity on cockroaches.

Test Example 3

Biological Test

The compound produced in Example 4 was assessed by a biological test using the linear track olfactometer at doses ranging from $10^{-3}$ pg to $10^3$ pg to determine the attraction-aggregation activity on cockroaches.

Figure 4:
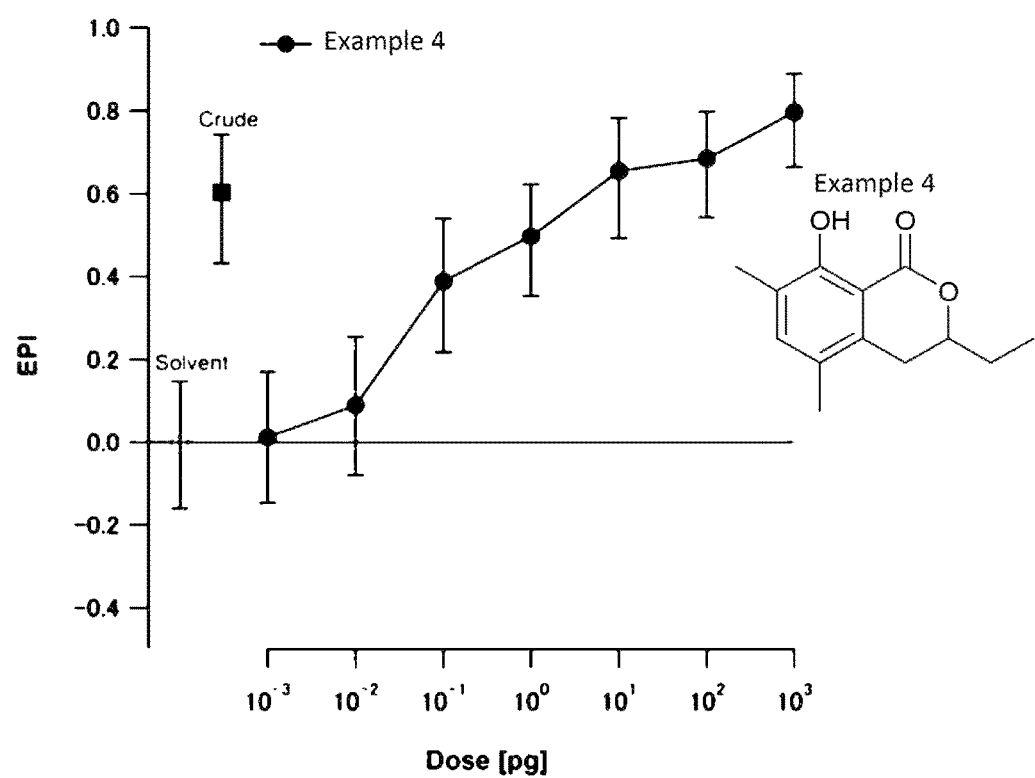
FIG. 4 is a chart showing the results of the biological test for determining attraction-aggregation activity on cockroaches using the linear track olfactometer in Test Example 3.

FIG. 4 shows the results of the biological test in Test Example 3 (Example 4).

The compound of Example 4 as a practical embodiment of the present invention showed high attraction-aggregation activity on cockroaches.

Test Example 4

Biological Test

Each of the compounds produced in Example 17 and Example 18 was assessed by a biological test using the linear track olfactometer at doses ranging from $10^{-3}$ pg to $10^6$ pg to determine the attraction-aggregation activity on cockroaches.

Figure 5:
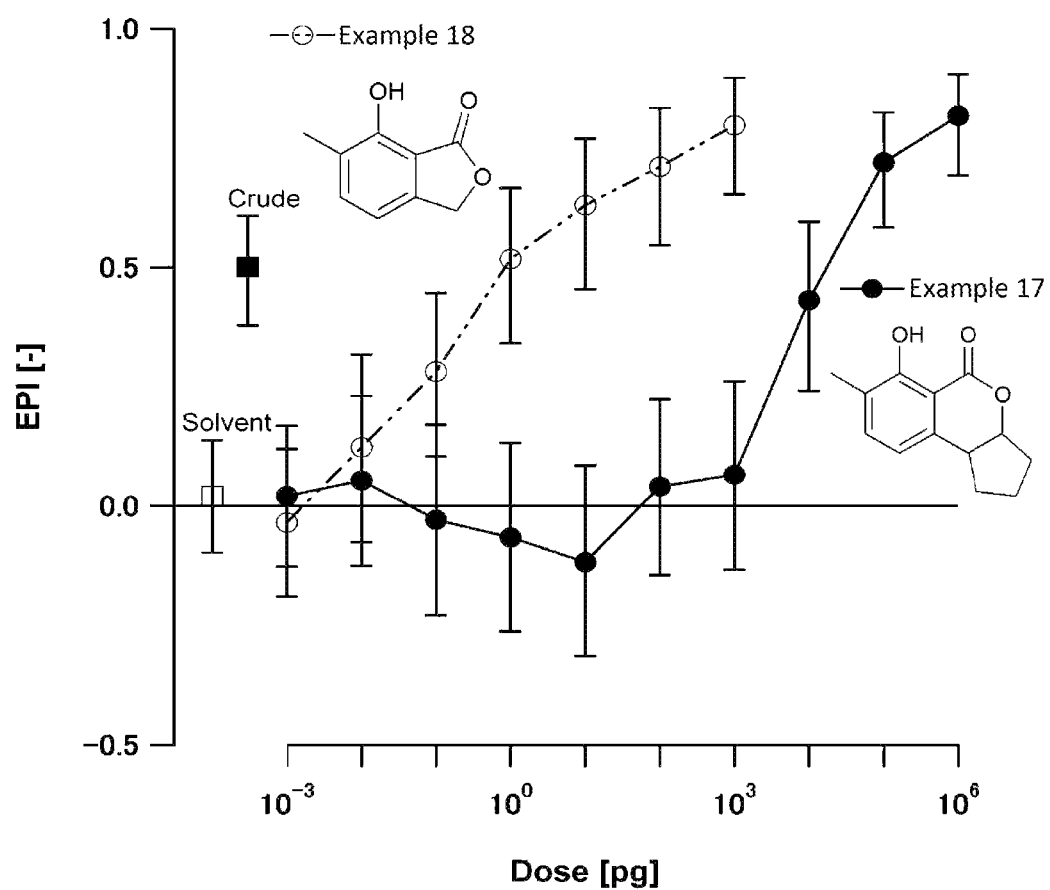
FIG. 5 is a chart showing the results of the biological test for determining attraction-aggregation activity on cockroaches using the linear track olfactometer in Test Example 4.

FIG. 5 shows the results of the biological test in Test Example 4 (Example 17 and Example 18).

The compounds produced in Example 17 and Example 18 as practical embodiments of the present invention showed attraction-aggregation activity on cockroaches, but the activity was lower than that of the compound of Example 18.

Example 24

Production of Cockroach Attraction-aggregation Substances (Cockroach Aggregation Pheromones) from Frass of American Cockroaches The cockroach attraction-aggregation substances of the present invention were produced from the frass of American cockroaches by the following steps (1) to (10).

Step (1)

The frass of American cockroaches were collected from the cages where the larvae or adults of American cockroaches were kept, and were frozen and stored at −20° C. as a material for producing attraction-aggregation substances. One kg of the sample was packed in a 5-L glass column and subjected to sequential extraction with 10 L of different solvents. Briefly, the sample was washed with 100% n-hexane under reduced pressure, and extraction was performed by passing a mixed solution of methanol/dichloromethane (1/99 (v/v)) through the column by gravity flow. Finally, the substances remaining in the column were eluted with 100% methanol. The fractions were assessed by the biological test using the linear track olfactometer to determine the attraction-aggregation activity on young larvae of American cockroaches. Intense activity was found in the methanol/dichloromethane (1/99 (v/v)) fraction. Hereinafter, this fraction is called crude extract.

Step (2)

The crude extract was dried and redissolved in 100% dichloromethane. To the solution, a 1 N sodium carbonate aqueous solution was added in the same volume as that of the above 100% dichloromethane, and the mixture was subjected to liquid-liquid partition in a conventional manner to give a dichloromethane fraction and an acidic fraction. The fractions were assessed by the biological test. Intense activity was found in the dichloromethane fraction.

Step (3)

The dichloromethane fraction was subjected to sequential elution in a silica gel open column (Wakogel C-200, Wako Pure Chemical Industries, Ltd.). Briefly, the sample was mixed with silica gel in an amount three times the weight of the solute and with calcined diatomaceous earth (Celite 545, Nacalai Tesque) in the same amount as that of the silica gel to give a suspension. The suspended sample was dried with a rotary evaporator to give a powder. The dried sample was loaded on the silica gel packed in the column in an amount ten times the weight of the solute. The sample was fractionated by sequential elution with three different solvents each in a volume about 200 times the weight of the solute. The fractions eluted with a mixed solution of dichloromethane/n-hexane (10/90 (v/v)), with a mixed solution of ethyl acetate/n-hexane (5/95 (v/v)) and with 100% ethyl acetate were assessed by the biological test. Intense activity was found in the ethyl acetate/n-hexane (5/95 (v/v)) fraction.

The ethyl acetate/n-hexane (5/95 (v/v)) fraction was purified again on a silica gel open column. Sequential elution from the support in an amount 30 times the weight of the solute was performed with a mixed solution of dichloromethane/n-hexane (20/80 (v/v)), then a mixed solution of ethyl acetate/n-hexane (1/99 (v/v)), and then 100% ethyl acetate, each in a volume 600 times the weight of the solute. The activity was observed only in the ethyl acetate/n-hexane (1/99 (v/v)) fraction.

Step (4)

The solvent was removed from the ethyl acetate/n-hexane (1/99 (v/v)) fraction. The resulting solid was dissolved in acetone in a volume 60 times the weight of the solid (60 mL of acetone relative to 1 g of the solid), and activated carbon was added in an amount three times the weight of the solid. The mixture was allowed to stand overnight. The activated carbon was filtered off, being washed with acetone in a volume 120 times the weight of the solid, to give an acetone fraction. The activated carbon after filtration was immersed in toluene in a volume 60 times the weight of the solid, and was allowed to stand overnight. The activated carbon was filtered off, being washed with toluene in a volume 120 times the weight of the solid, to give a toluene fraction. The biological test showed intense activity in the acetone fraction.

Step (5)

The acetone fraction was purified on an open column filled with porous polymer beads (CHP20P, Mitsubishi Chemical Corporation). Briefly, the sample was dried and redissolved in 100% methanol. The solution was mixed with polymer beads in an amount three times the amount of the solute, and the suspension was loaded on the column. Sequential elution was performed with methanol/water (0/100 (v/v)), then methanol/water (85/15 (v/v)), then methanol/water (95/5 (v/v)), and then 100% methanol. The eluates were concentrated and then redissolved in dichloromethane. The biological test showed intense activity in the methanol/water (95/5 (v/v)) fraction.

Step (6)

The solvent was removed from the methanol/water (95/5 (v/v)) fraction, which contained active compounds. The resulting solid was subjected to sequential elution on a silica gel open column filled with silica gel (Wakogel C-200, Wako Pure Chemical Industries, Ltd.) in a weight 60 times the weight of the solid (solute). Before loaded on the column, the solute was redissolved in 10 mL of 10% ethyl acetate/n-hexane. The eluting solvents used were ethyl acetate/n-hexane (5/95 (v/v)) and then ethyl acetate. The volume of each eluting solvent was 600 times that of the solute. The biological test showed intense activity in the ethyl acetate/n-hexane (5/95 (v/v)) fraction.

Step (7)

The ethyl acetate/n-hexane (5/95 (v/v)) fraction obtained in step (6) was further purified by HPLC (LC-10AT, Shimadzu Corporation). Briefly, the fraction was purified by normal-phase HPLC using a silica gel column (COSMOSIL 5SL-II, Nacalai Tesque, 4.6 mm diameter×150 mm). The mobile phase solvent was ethyl acetate/n-hexane (5/95 (v/v)) (1 mL/min). The absorption at 254 nm was monitored with a UV detector (SPD-10MAVP, Shimadzu Corporation). The fractions were collected at every 0.5 minutes. The physiological activity of the fractions was determined, and four active fractions were obtained (active fractions I to IV).

Step (8)

Each of the four active fractions (active fractions I to IV) obtained in step (7) was purified by reversed-phase HPLC on an ODS column (COSMOSIL 5AR-II, Nacalai Tesque, 4.6 mm diameter×150 mm). The mobile phase was 100% methanol. The sample was slowly eluted at 0.2 mL/min. The sample was fractionated as described above, and the resulting fractions were assessed by the biological test. Fractions having high activity were subjected to the next step.

Step (9)

Each of the fractions was further purified on a COSMOSIL πNAP column (4.6 mm diameter×150 mm, Nacalai Tesque). The πNAP is a stationary phase prepared by chemically modifying a silica gel support with a naphthyl group. The mobile phase was isopropanol/methanol (50/50 (v/v)) (0.2 mL/min). The sample was fractionated while monitoring UV absorption peaks. The resulting fractions were assessed by the biological test. Fractions having high activity were subjected to the next step.

Step (10)

Each of the fractions obtained in step (9) was purified again by normal-phase HPLC on a silica gel column using ethyl acetate/n-hexane (0.5/99.5 (v/v)). Fractions with appreciable UV absorption peaks were collected (active fractions I to IV) and assessed by the biological test to determine fractions with high activity. The solvents were removed from the fractions with high activity to give cockroach attraction-aggregation substances.

The cockroach attraction-aggregation substances obtained in step (10) were analyzed by NMR, and in total, six compounds were identified. From active fraction I, two compounds were identified (called PLD-F and PLD-E). From active fraction II, one compound was identified (called PLD-D). From the active fraction III, one compound was identified (called PLD-C). From the active fraction IV, two compounds were identified (called PLD-B and PLD-A).

Figure 6:
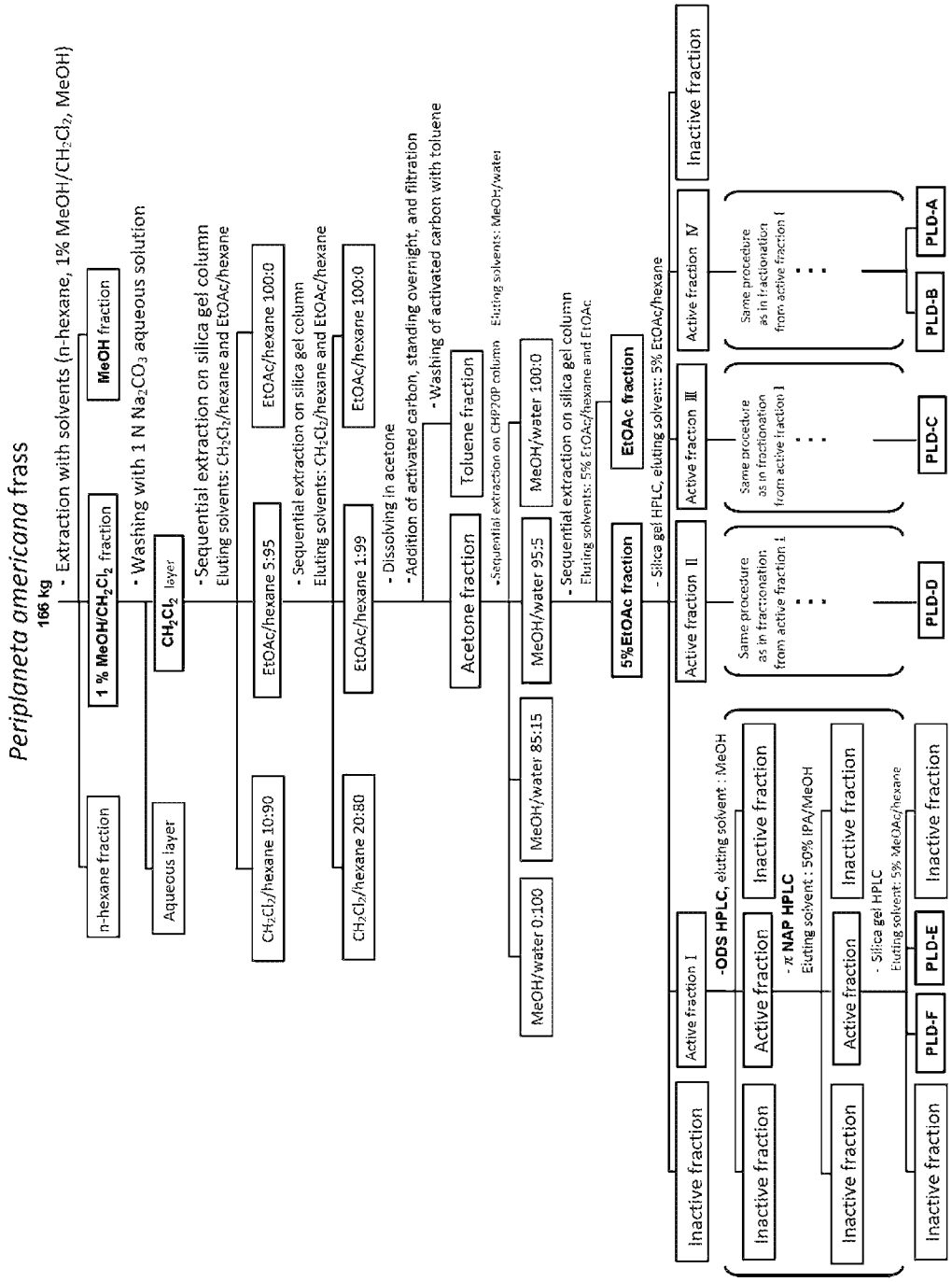
FIG. 6 is the flowchart of the procedure in Example 24 where the cockroach attraction-aggregation substances of the present invention were produced by extraction from the frass of American cockroaches. In the flowchart, MeOH means methanol, EtOAc means ethyl acetate, IPA means isopropanol, MeOAc means methyl acetate, active fraction means a fraction exhibiting attraction-aggregation activity on cockroaches in a biological test, and inactive fraction means a fraction lacking attraction-aggregation activity on cockroaches in a biological test.

FIG. 6 shows the flowchart of the procedure of this test.

The chemical structural formulae, NMR data, and MS data of the identified compounds PLD-A, PLD-B, PLD-C, PLD-D, PLD-E and PLD-F are shown below. The arrows in the structural formulae indicate NOE correlations observed in NOESY measurement.

PLD-A: (trans)-3,4-dihydro-8-hydroxy-3,4,7-trimethyl-1H-2-benzopyran-1-one

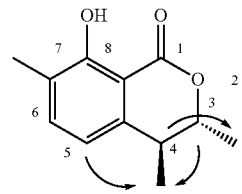

$^1$H-NMR (500 MHz, CDCl$_3$, ppm): δ11.41 (s, 1H, C8-OH), 7.34 (d, j=7.60 Hz, 1H, C6-H), 6.68 (d, j=7.10 Hz, 1H, C5-H), 4.48 (quip, j=6.58 Hz, 1H, C3-H), 2.86 (quip, j=6.99 Hz, 1H, C4-H), 2.26 (s, 3H, C7-CH$_3$), 1.48 (d, j=6.40 Hz, 3H, C3-CH$_3$), 1.35 (d, j=7.05 Hz, 3H, C4-CH$_3$)

$^{13}$C-NMR (125 MHz, CDCl$_3$, ppm): δ169.66 (—C=O), 160.58 (C), 141.20 (C), 137.07 (CH), 125.23 (C), 115.80 (CH), 106.94 (C), 81.09 (CH), 37.26 (CH), 19.69 (CH$_3$), 17.26 (CH$_3$), 15.42 (CH$_3$)

EI-MS: 206 (M$^+$, 100%), 191 (M$^+$-CH$_3$, 7) 188 (M$^+$-H$_2$O, 16), 177 (49), 173 (188-CH$_3$, 14), 162 (72), 145 (10), 134 (20)

The $^1$H-NMR spectrum data of this compound were identical with those of the compound obtained in the organic synthesis in Example 7.

PLD-B: (cis)-3,4-dihydro-8-hydroxy-3,4,7-trimethyl-1H-2-benzopyran-1-one

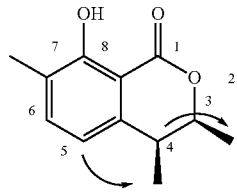

$^1$H-NMR (500 MHz, CDCl$_3$, ppm): δ11.27 (s, 1H, C8-OH), 7.30 (d, j=7.50 Hz, 1H, C6-H), 6.62 (d, j=7.50 Hz, 1H, C5-H), 4.76 (dq, j=3.26, 6.58 Hz, 1H, C3-H), 2.90 (dq, j=3.49, 7.14 Hz, 1H, C4-H), 2.25 (s, 3H, C5-CH$_3$), 1.44 (d, j=6.60 Hz, 3H, C3-CH$_3$), 1.20 (d, j=7.10 Hz, 3H, C4-CH$_3$)

$^{13}$C-NMR (125 MHz, CDCl$_3$, ppm): δ170.34 (—C=O), 160.47 (C), 143.57 (C), 137.03 (CH), 125.11 (C), 116.37 (CH), 106.56 (C), 78.31 (CH), 36.44 (CH), 17.19 (CH$_3$), 15.43 (CH$_3$), 14.51 (CH$_3$)

EI-MS: 206 (M$^+$, 100%), 191 (M$^+$-CH$_3$, 6) 188 (M$^+$-H$_2$O, 18), 177 (88), 173 (188-CH$_3$, 35), 162 (61), 145 (12), 134 (23)

The $^1$H-NMR spectrum data of this compound were identical with those of the compound obtained in the organic synthesis in Example 8.

PLD-C: (trans)-3,4-dihydro-8-hydroxy-4,7-dimethyl-3-ethyl-1H-2-benzopyran-1-one

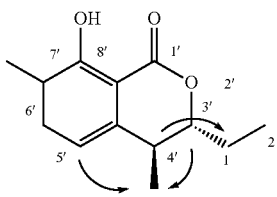 [SMILES: CC[C@H]1OC(=O)C2=C(O)C(C)CC=C2[C@@H]1C]

$^1$H-NMR (500 MHz, CDCl$_3$, ppm): δ11.39 (s, 1H, C8'-OH), 7.30 (d, j=7.55 Hz, 1H, C6'-H), 6.66 (d, j=7.55 Hz, 1H, C5'-H), 4.29 (dt, j=7.55, 5.40 Hz, 1H, C3'-H), 2.93 (quin, j=6.71 Hz, 1H, C4'-H), 2.24 (s, 3H, C7'-CH$_3$) 1.77 (m, 1H, C1-H), 1.75 (m, 1H, C1-H), 1.34 (d, j=7.05 Hz, 3H, C4'-CH$_3$), 1.05 (t, j=7.40 Hz, 3H, C2)

$^{13}$C-NMR (125 MHz, CDCl$_3$, ppm): δ169.57 (—C=O), 160.51 (C), 141.44 (C), 137.04 (CH), 125.13 (C), 116.12 (CH), 106.93 (C), 85.94 (CH), 35.03 (CH), 26.31 (CH$_2$), 18.29 (CH$_3$), 15.42 (CH$_3$), 9.43 (CH$_3$)

EI-MS: 220 (M$^+$, 100%), 202 (M$^+$-H$_2$O, 16), 191 (M$^+$-C$_2$H$_5$, 22), 187 (188-CH$_3$, 25), 177 (41), 162 (81), 145 (6), 134 (17)

The $^1$H-NMR spectrum data of this compound were identical with those of the compound with lower polarity obtained in the organic synthesis in step 6-3 of Example 6.

PLD-D: (cis)-3,4-dihydro-8-hydroxy-4,7-dimethyl-3-ethyl-1H-2-benzopyran-1-one

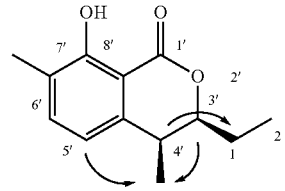 [SMILES: CC[C@@H]1OC(=O)c2c(ccc(C)c2O)[C@@H]1C]

$^1$H NMR (500 MHz, CDCl$_3$, ppm): δ11.26 (s, 1H, C8'-OH), 7.30 (d, j=7.50 Hz, 1H, C6'-H), 6.62 (d, j=7.50 Hz, 1H, C5'-H), 4.46 (m, 1H, C3'-H), 2.92 (dq, j=7.09, 2.94 Hz, 1H, C4'-H), 2.24 (s, 3H, C7'-CH$_3$) 1.92 (m, 1H, C1-H), 1.69 (m, 1H, C1-H), 1.16 (d, j=7.20 Hz, 3H, C4'-CH$_3$), 1.07 (t, j=7.45 Hz, 3H, C2)

$^{13}$C NMR (125 MHz, CDCl$_3$, ppm): δ170.50 (—C=O), 160.40 (C), 144.10 (C), 137.00 (CH), 125.00 (C), 116.46 (CH), 106.76 (C), 83.62 (CH), 35.21 (CH), 24.63 (CH$_2$), 15.42 (CH$_3$), 14.70 (CH$_3$), 9.76 (CH$_3$)

EI-MS: 220 (M$^+$, 100%), 202 (M$^+$-H$_2$O, 14), 191 (M$^+$-C$_2$H$_5$, 22), 187 (188-CH$_3$, 30), 177 (82), 162 (66), 145 (5), 134 (16)

The $^1$H-NMR spectrum data of this compound were identical with those of the compound obtained in the organic synthesis in Example 9.

PLD-E: 3,4-dihydro-8-hydroxy-3-(1-methylpropyl)-5,7-dimethyl-1H-2-benzopyran-1-one

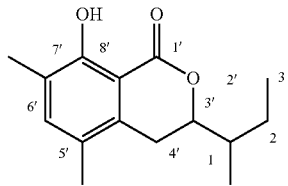 [SMILES: CCC(C)C1Cc2c(C)cc(C)c(O)c2C(=O)O1]

$^1$H-NMR (500 MHz, CDCl$_3$, ppm): δ11.23 (s, 1H, C8'-OH), 7.26 (s, 1H, C6'-H), 4.36 (ddd, j=3.50, 6.10, 12.00 Hz, 1H, C3'-H), 2.82 (dd, j=3.50, 16.40 Hz, 1H, C4'-H), 2.73 (dd, j=12.00, 16.50 Hz, 1H, C4'-H), 2.22 (s, 3H, C7'-CH$_3$), 2.17 (s, 3H, C5'-CH$_3$), 1.89 (m, 1H, C1-H), 1.68 (m, 1H, C2-H), 1.34 (m, 1H, C2-H), 1.04 (d, j=6.85 Hz, 3H, C1-CH$_3$), 0.97 (t, j=7.45 Hz, 3H, C3)

$^{13}$C-NMR (125 MHz, CDCl$_3$, ppm): δ170.95 (—C=O), 158.86 (C), 138.83 (CH), 134.46 (C), 124.55 (C), 124.18 (C), 107.77 (C), 82.69 (CH), 38.47 (CH), 26.45 (CH$_2$), 24.84 (CH$_2$), 17.98 (CH3), 15.30 (CH$_3$), 14.37 (CH$_3$), 11.34 (CH$_3$)

EI-MS: 248 (M$^+$, 100%), 230 (M$^+$-H$_2$O, 12), 215 (230-CH$_3$, 14), 212 (27), 201 (35), 197 (17), 191 (28), 179 (29), 163 (51), 145 (5), 133 (14)

The $^1$H-NMR spectrum data of this compound were identical with those of the compound obtained in the organic synthesis in Example 10.

PLD-F: 3,4-dihydro-8-hydroxy-3-(1-methylbutyl)-5,7-dimethyl-1H-2-benzopyran-1-one

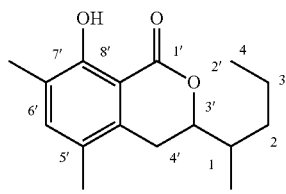

$^1$H-NMR (500 MHz, CDCl$_3$, ppm): δ11.23 (s, 1H, C8'-OH), 7.16 (s, 1H, C6'-H), 4.36 (ddd, j=3.63, 5.83, 11.98 Hz, 1H, C3'-H), 2.79 (dd, j=3.55, 16.40 Hz, 1H, C4'-H), 2.73 (dd, j=11.90, 16.50 Hz, 1H, C4'-H), 2.22 (s, 3H, C7'-CH$_3$), 2.17 (s, 3H, C5f-CH$_3$), 1.97 (m, 1H, C1-H), 1.35-1.21 (m, 4H, C2-H and C3-H), 1.05 (d, j=6.80 Hz, 3H, C1-CH$_3$), 0.97 (t, j=7.10 Hz, 3H, C4)

$^{13}$C-NMR (125 MHz, CDCl$_3$, ppm): δ170.98 (—C=O), 158.87 (C), 138.83 (CH), 134.49 (C), 124.54 (C), 124.17 (C), 107.77 (C), 82.98 (CH), 36.65 (CH), 34.28 (CH$_2$), 26.35 (CH$_2$), 20.14 (CH$_2$), 17.99 (CH$_3$), 15.30 (CH$_3$), 14.79 (CH$_3$), 14.11 (CH$_3$)

EI-MS: 262 (M$^+$, 100%), 244 (M$^+$-H$_2$O, 7), 229 (244-CH$_3$, 19), 226 (22), 211 (19), 201(31), 191 (39), 179 (31), 163 (58), 145 (6), 133 (15)

The $^1$H-NMR spectrum data of this compound were identical with those of the compound obtained in the organic synthesis in Example 11.

Test Example 5

Biological Test

Each of the compounds PLD-A, PLD-B, PLD-C, PLD-D, PLD-E, and PLD-F obtained in Example 24 was assessed by the biological test using the linear track olfactometer to determine the attraction-aggregation activity on cockroaches.

Figure 7:
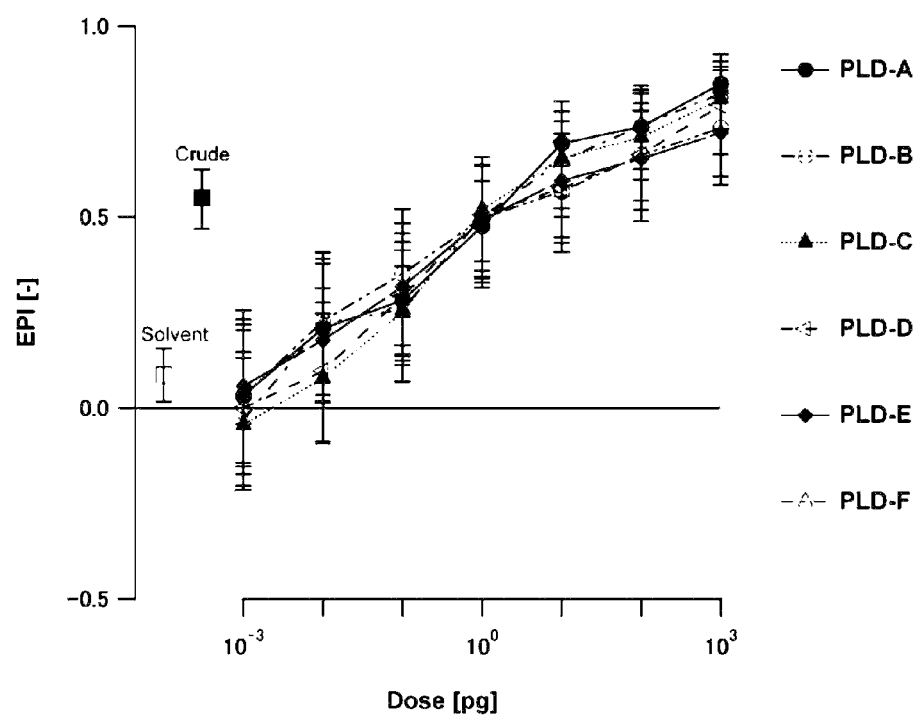
FIG. 7 is a chart showing the results of the biological test for determining attraction-aggregation activity on cockroaches using the linear track olfactometer in Test Example 5.

FIG. 7 shows the results of the biological test in Test Example 5 (Example 24).

The compounds PLD-A, PLD-B, PLD-C, PLD-D, PLD-E, and
PLD-F as practical embodiments of the present invention showed high attraction-aggregation activity on cockroaches.

Test Example 6

Biological Test (Semi-practical Test)

A solution of 0.5 μg of a test compound or a control compound in 0.5 mL of ethanol was impregnated in a cotton pad of 1.2 cm square. The cotton pad was air-dried for 30 minutes. The dried cotton pad was placed at the center of the adhesive face of a sticky cockroach trap (trade name "Gokiburi Catcher", produced by Dainihon jochugiku Co., Ltd.) to prepare a test sample or a control sample.

The test compounds were PLD-A, PLD-C, PLD-E, Example 20, Example 21, and no compound.

The control compound was sotolon (3-hydroxy-4,5-dimethyl-2[5H]-furanone, produced by Wako Pure Chemical Industries, Ltd.), which is known as an active compound with cockroach-attracting activity (Nippon Nogeikagaku Kaishi, Vol. 57, 655-658, 1983).

In experiments for American cockroaches, a test area with a size of 2 m 98 cm×1 m 70 cm×height 20 cm was prepared. Three pieces of pleated filter paper of 30 cm square were stacked one another and placed at the center of the test area to provide a shelter. Two water cups were placed at two opposite sides of the shelter. In experiments for smokybrown cockroaches and German cockroaches, a clothes box with a size of 55 cm×38 cm×height 30 cm was used as a test area. Three pieces of pleated filter paper of 15 cm square were stacked one another and placed at the center of the test area to provide a shelter. Two water cups were placed at two opposite sides of the shelter.

In experiments for American cockroaches and smokybrown cockroaches, five female adults, five male adults, 10 middle- or late-stage larvae, and 20 early-stage larvae were simultaneously released. In experiments for German cockroaches, 10 female adults, 10 male adults, 20 middle- or late-stage larvae, and 20 early-stage larvae were simultaneously released. Each test area was then left overnight. The next day, two test samples were placed at the diagonally opposite corners in each test area, and two control samples were placed at the other diagonally opposite corners. The test area was then left overnight.

The next day, the number of cockroaches that were attracted to each sample and captured by the trap was counted. The relative number of the captured cockroaches was calculated taking the number of cockroaches that were attracted to sotolon (control sample) and captured by the trap as 1.

Figure 8:
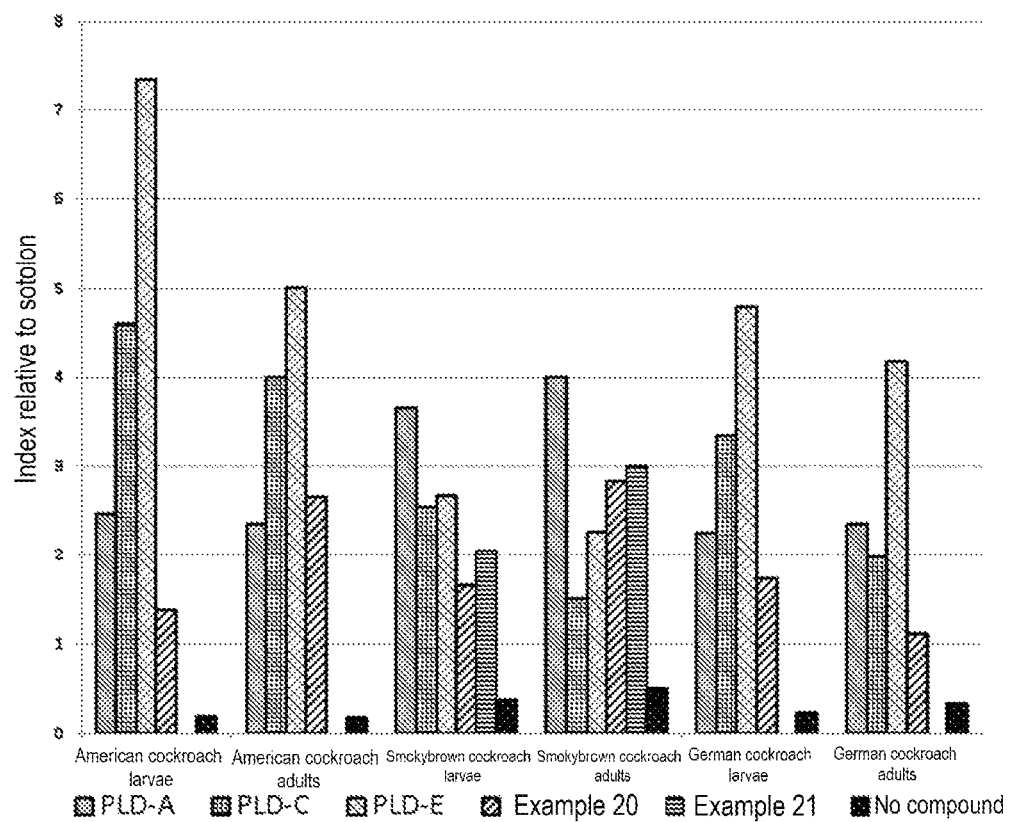
FIG. 8 is a chart showing the results of the semi-practical test for determining attraction-aggregation activity on cockroaches using a sticky cockroach trap in Test Example 6.

The results are shown in FIG. 8.

All the test compounds had larger numbers of the captured cockroaches than that for sotolon, which is known as an active compound with cockroach-attracting activity. The results indicated that all the test compounds are excellent in the attraction-aggregation effect. The effect varied with the species, but all the test compounds were effective for all the species, i.e., American cockroaches, smokybrown cockroaches, and German cockroaches.

Specific examples of various formulations using the cockroach attraction-aggregation substance of the present invention will be described below. In the following Examples, the term "part" means "part by weight".

Example 25

Production of Poisoned Baits

To a mixture of 5 parts of hydramethylnon, 15 parts of boric acid, 10 parts of skim milk, 5 parts of sesame oil, 15 parts of glycerol, 25 parts of starch, 20 parts of rice bran and 5 parts of purified water was added (trans)-3,4-dihydro-8-hydroxy-4,7-dimethyl-3-ethyl-1H-2-benzopyran-1-one (the compound with lower polarity in step 6-3 of Example 6 or the compound referred to as PLD-C) or 3,4-dihydro-8-hydroxy-3,7-dimethyl-1H-2-benzopyran-1-one (the compound of step 1-4 of Example 1) in an amount of 0.1 ppm. The mixture was homogenously kneaded and extruded into about 10 g of pellets to give poisoned baits.

Example 26

Production of Trap

To a mixture prepared by kneading 30 parts of rice bran, 15 parts of fish powder, and 50 parts of a starch sizing agent with 5 parts of purified water was added 3,4-dihydro-8-hydroxy-3-(1-methylpropyl)-5,7-dimethyl-1H-2-benzopyran-1-one (the compound referred to as PLD-E in Example 10) or 3,4-dihydro-8-hydroxy-3-ethyl-6,7-dimethyl-1H-2-benzopyran-1-one (the compound of Example 5) so that the amount per tablet would be 100 ppm. The mixture was punched into a disc shape with 15 mm in diameter and 2 mm in thickness to give tablets (weight: 1 g).

Next, an adhesive composition containing 95 parts of polybutene (molecular weight: 900) and 5 parts of polyisobutylene (molecular weight: 1,200,000) was prepared. The composition was applied to a cardboard with a size of length 8 cm×width 15 cm×thickness 1 mm so that the thickness of the adhesive would be 0.5 mm to give an adhesive plate. The tablets prepared above was placed at the center of the adhesive plate to give a cockroach-attracting trap.

INDUSTRIAL APPLICABILITY

The cockroach attraction-aggregation substance according to the present invention exhibited excellent attraction-aggregation activity on American cockroaches as well as on smokybrown cockroaches and German cockroaches.

The cockroach attraction-aggregation substance can be used to provide a cockroach attractant or a cockroach controlling agent. The compounds according to the present invention not only exhibit attraction-aggregation activity on cockroaches but also serve as potential active substances for attracting ants. Therefore the compounds of the present invention are highly useful.

REFERENCE SIGNS LIST

1 Suction outlet
2a Inlet (control side)
2b Inlet (sample side)
3 Metal disc coated with a sample
4 Location for placing insect subjects

The invention claimed is:

1. A cockroach attraction-aggregation compound, the compound being represented by general formula:

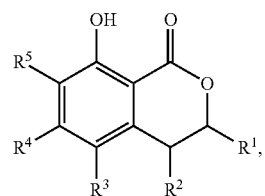

(I)

wherein $R^1$ to $R^4$ are each independently selected from the group consisting of a hydrogen atom, a halogen atom, an optionally substituted ($C_1$-$C_6$)alkyl group, an optionally substituted ($C_3$-$C_6$)cycloalkyl group, an optionally substituted ($C_2$-$C_6$)alkenyl group, and an optionally substituted ($C_2$-$C_6$)alkynyl group;
wherein $R^5$ is an unsubstituted methyl group,
wherein two of $R^2$, $R^3$ and $R^4$ are hydrogen atoms and the other is selected from the group consisting of an optionally substituted ($C_1$-$C_6$)alkyl group, an optionally substituted ($C_3$-$C_6$)cycloalkyl group, an optionally substituted ($C_2$-$C_6$)alkenyl group, and an optionally substituted ($C_2$-$C_6$)alkynyl group, and
provided that in the case where $R^1$ is methyl, $R^2$ is a hydrogen atom, and $R^3$ and $R^4$ are each independently a hydrogen atom or methyl is excluded, in the case where $R^1$ is ethyl or 2-hydroxyl-1-propyl, $R^2$, $R^3$ and $R^4$ are each a hydrogen atom is excluded, in the case where $R^1$ is ethyl, $R^2$ and $R^4$ are each a hydrogen atom, and $R^3$ is methyl is excluded, in the case where $R^1$ is ethyl, $R^2$ and $R^3$ are each a hydrogen atom, and $R^4$ is methyl is excluded, and in the case where $R^1$ is hydrogen atom, and $R^2$, $R^3$ and $R^4$ are each independently a methyl is excluded, or
a salt thereof.

2. The compound according to claim 1 or a salt thereof, wherein $R^1$ is a group selected from the group consisting of an optionally substituted ($C_1$-$C_6$)alkyl group, an optionally substituted ($C_3$-$C_6$)cycloalkyl group, an optionally substituted ($C_2$-$C_6$)alkenyl group, and an optionally substituted ($C_2$-$C_6$)alkynyl group.

3. The compound of the formula (I) of claim 1 being represented by the following formula:

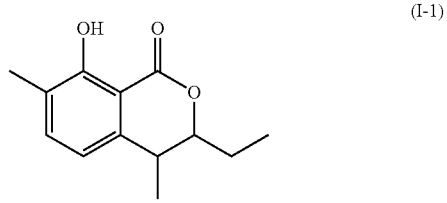

(I-1)

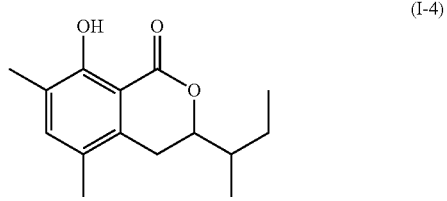

(I-4)

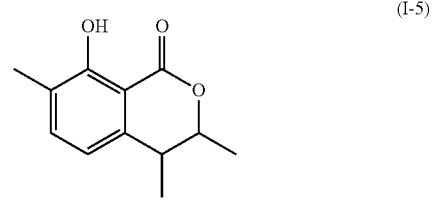

(I-5)

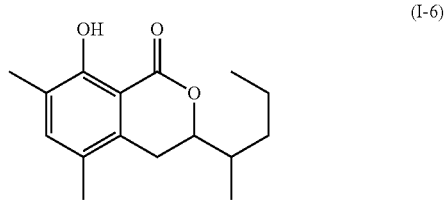

(I-6)

or
a salt thereof.

4. A compound represented by the following formula:

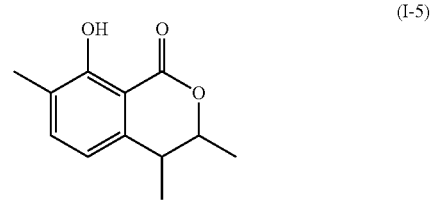

(I-5)

or
a salt thereof.

* * * * *